(12) United States Patent
Blech et al.

(10) Patent No.: US 6,492,377 B1
(45) Date of Patent: Dec. 10, 2002

(54) IMIDAZOTRIAZOLOPYRIMIDINES WITH ADENOSINE-ANTAGONISTIC ACTIVITY

(75) Inventors: Stefan Blech, Warthausen (DE); Adrian Carter, Bingen (DE); Wolfram Gaida, Ingelheim (DE); Matthias Hoffmann, Ingelheim (DE); Ulrike Kuefner-Muehl, Ingelheim (DE); Christopher John Montague Meade, Bingen (DE); Gerald Pohl, Gau-Algesheim (DE); Werner Kummer, Ingelheim (DE); Erich Lehr, Waldalgesheim (DE); Joachim Mierau, Mainz (DE); Thomas Weiser, Nieder-Olm (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/559,806

(22) Filed: Apr. 26, 2000

Related U.S. Application Data

(63) Continuation-in-part of application No. 09/333,621, filed on Jun. 15, 1999, now abandoned, and a continuation-in-part of application No. 09/333,408, filed on Jun. 15, 1999, which is a continuation-in-part of application No. PCT/EP98/05455, filed on Aug. 27, 1998.
(60) Provisional application No. 60/090,587, filed on Jun. 25, 1998, and provisional application No. 60/090,586, filed on Jun. 25, 1998.

(51) Int. Cl.⁷ ............... C07D 487/14; C07D 249/00; C07D 239/00; C07D 235/00; A61K 31/495
(52) U.S. Cl. ........................ 514/267; 544/251
(58) Field of Search .................. 514/251; 544/267

(56) References Cited

FOREIGN PATENT DOCUMENTS

DE 196 29 378 A 1/1998

OTHER PUBLICATIONS

DeNinno, M.P., Annual Reports in Medicinal Chemistry, 33, 1998, 111–120.*
Tenor (Chem.Ber.), 97, 1964, 1373–1382.*
McEntee WJ, Larrabee GJ, Curr Treat Options Neurol 2000 Jan.; 2(1):73–80. abstract only.*
Deckert, J. et al, Neuroscience Letters, 224, 1998, 1–4.*
Mueller, C.E.; Stein, B. *Current Pharmaceutical Design*, 1996, 2, 501–530.
Fiebich, B.L.; Biber, K.; Gyufko, K.; Berger, M.; Bauer, J.; van Calker, D., *J. Neurochem.*, 1996, 66, 1426.
Mueller, C.E., Exp. Opin. Ther. Patents (1997)7(5):419–440.
Haas, H.L.; Selbach, O., *Naunyn–Schmiedebergs' Ach Pharmacol* (2000) 362:375–381.
Tenor, Et Al; 1,2,4–Triazoles, Synthesis and reactivity of –amino–s–triazolo[1,5–a]–5pyrimidones, Chem., Ber. 97(5), 1373–82 (1964).

* cited by examiner

*Primary Examiner*—Mukund J. Shah
*Assistant Examiner*—Thomas McKenzie

(57) ABSTRACT

New imidazotriazolopyrimidine derivatives of the formula

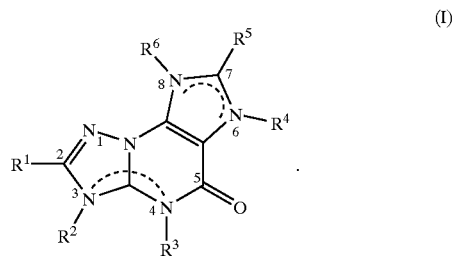

Preferred are those compounds wherein:

$R^1$ denotes methyl, which is optionally substituted by phenyloxy or pyrrole; or $R^1$ denotes benzyl which is optionally substituted by hydroxy, methoxy, dimethylaminoethoxy or fluorine; or $R^1$ denotes cyclopentyl, furan or phenylethyl;

$R^2$ or $R^3$ denote ethyl, n-propyl, allyl or propargyl;

$R^4$ or $R^6$ denote hydrogen; and, $R^5$ denotes methyl, n-propyl, tert.butyl, cyclopentyl or norbornenyl.

These are adenosine antagonists are are useful for, inter alia, the treatment of senile dementia of the Alzheimer's type.

11 Claims, No Drawings

IMIDAZOTRIAZOLOPYRIMIDINES WITH ADENOSINE-ANTAGONISTIC ACTIVITY

RELATED APPLICATIONS

This application is a continuation-in-part of International Application No. PCT/EP98/05455, filed Aug. 27, 1998, U.S. application Ser. No. 09/333,621, filed Jun. 15, 1999 now abandoned, and U.S. application Ser. No. 09/333,408, filed Jun. 15, 1999. The benefit of prior provisional applications Serial Nos. 60/090,587, filed Jun. 25, 1998 and No. 60/090,586, filed Jun. 25, 1998, are hereby claimed.

FIELD OF THE INVENTION

The invention relates to new imidazotriazolopyrimidines, processes for preparing them, pharmaceutical compositions comprising such compounds, and their use as medicaments for the treatment of various disease conditions.

BACKGROUND OF THE INVENTION

It is known that adenosine antagonists may have a therapeutically useful effect in the treatment of diseases or pathological conditions that are somehow caused by activation of adenosine receptors.

Adenosine is an endogenous modulator with predominantly inhibitory effects in the CNS, in the heart, in the kidneys and other organs. The effects of adenosine are mediated via at least three receptor sub-types: adenosine $A_1$, $A_2$ and $A_3$ receptors. Adenosine $A_2$ receptors are further subdivided into two subtypes, $A_{2a}$ and $A_{2b}$. The two $A_2$ receptor subtypes can be differentiated, e.g. because specific adenosine antagonists such as CGS 21680 stimulate predominantly only the $A_{2a}$ subtype. It is presumed that the $A_{2b}$ subtype has a relatively low affinity for adenosine. For this reason, relatively high concentrations of adenosine are necessary in order to stimulate this subtype. Such high concentrations would be expected, for example, in the epithelial surface fluid in the lungs of asthmatics or in ischaemic tissue damage.

In the CNS, adenosine develops inhibitory effects mainly by activating $A_1$ receptors: presynaptically by inhibiting the synaptic transmission (inhibiting the release of neurotransmitters such as acetylcholine, dopamine, noradrenaline, serotonin, glutamate, etc.), and postsynaptically by inhibiting neuronal activity.

$A_1$ antagonists cancel out the inhibitory effects of adenosine and promote neuronal transmission and neuronal activity.

$A_1$ antagonists are therefore of great interest for treating degenerative diseases of the central nervous system such as senile dementia of the Alzheimer's type and age-related disorders of memory and learning capacity.

The disease includes, in addition to forgetfulness in its mild form and total helplessness and absolute dependence on care in its severe form, a number of other accompanying symptoms such as sleep disorders, motor co-ordination disorders ranging up to Parkinson's syndrome, in addition to increased emotional instability and depressive symptoms. The disease is progressive and can lead to death. The treatments used hitherto have been unsatisfactory. At present there are no specific therapeutic agents at all. Attempts at treatment with acetylcholinesterase inhibitors show an effect in only a small proportion of the patients, but involve a high level of side effects.

The pathophysiology of Alzheimer's disease and SDAT is characterised by a severe deterioration of the cholinergic system, but other transmitter systems are also affected. As a result of the loss of presynaptic cholinergic and other neurones and the resulting lack of preparation of neurotransmitters the neuronal transmission and neuronal activity in the areas of the brain essential for learning and memory are significantly reduced.

Selective adenosine $A_1$ receptor antagonists promote neuronal transmission by the increased production of neurotransmitters, increase the excitability of postsynaptic neurones and can therefore counteract the symptoms of the disease.

The high receptor affinity and selectivity of some of the compounds claimed ought to make it possible to treat Alzheimer's disease and SDAT with low doses, so that hardly any side effects need be expected which cannot be put down to the blockade of $A_1$ receptors.

Another indication for centrally-acting adenosine $A_1$ antagonists is depression. The therapeutic success of antidepressant substances appears to be linked to the regulation of $A_1$ receptors. $A_1$ antagonists may lead to the regulation of adenosine $A_1$ receptors and thus offer a new therapeutic approach to the treatment of depressive patients.

Other areas of use for $A_2$ selective adenosine antagonists, in particular, are neurodegenerative diseases such as Parkinson's disease and also migraine. Adenosine inhibits the release of dopamine from central synaptic endings by interacting with dopamine-$D_2$ receptors. $A_2$ antagonists increase the release and availability of dopamine and thus offer a new therapeutic approach to the treatment of Parkinson's disease.

In migraine, the vasodilatation of cerebral blood vessels mediated by $A_2$ receptors appears to be involved. Selective $A_2$ antagonists inhibit the vasodilatation and can therefore be useful in treating migraine.

Adenosine antagonists may also be used for treating peripheral indications.

For example, the activation of $A_1$, $A_2$ or $A_3$ receptors in the lung may lead to bronchoconstriction. Selective adenosine $A_1$ antagonists relax the tracheal smooth muscle, cause bronchodilatation and can thus be useful as antiasthmatic agents.

Adenosine $A_{2b}$ or $A_3$ receptors are located on mast cells. Their activation causes the release of mast cell products such as histamine, tryptase or interleukin 8. Adenosine $A_3$ receptors are found on eosinophiles and the stimulation of these receptors can influence the activation, chemotaxis and apoptosis of eosinophiles. Therefore, antagonists of $A_{2b}$ or $A_3$ receptors are very promising for the treatment of allergic diseases such as e.g. rhinitis, urticaria, pruritis, allergic dermatitis, allergic eye diseases and nasal polyps. In addition, the effect of adenosine $A_{2b}$ or $A_3$ antagonists on mast cells and eosinophiles may also be helpful in the treatment of asthma.

Furthermore, the anti-mast cell activity may be useful for reducing reperfusion damage after cardiac ischaemia.

By activating $A_2$ receptors, adenosine may cause, inter alia, respiratory depression and cessation of breathing. $A_2$ antagonists bring about respiratory stimulation. For example, adenosine antagonists (theophyllin) are used to treat respiratory distress and prevent sudden infant death in premature babies.

Adenosine stimulates the production of mucus by epithelial cells. The activation of adenosine $A_{2b}$ receptors on bronchial epithelial cells stimulates the chloride transportation which affects the consistency of mucus. Consequently, adenosine antagonists offer new therapeutic approaches to the treatment of diseases in which the quantity or consistency of the mucus is pathological, as in bronchitis and chronic obstructive pulmonary diseases, for example.

Adenosine $A_{2b}$ receptors are also located on the epithelial cells of the intestine. In the intestinal cells, too, the activation of these receptors can lead to increased chloride transportation. It is suspected that during inflammations of the intestines adenosine is released by neutrophiles, for example. The effect of the released adenosine on the chloride transportation influences the motility and absorption capacity of the intestinal epithelium. As a result, adenosine antagonists are possible therapeutic agents for inflammatory intestinal diseases and diarrhoea.

Other important therapeutic fields for adenosine antagonists are cardiovascular diseases and kidney diseases.

In the heart, adenosine inhibits electrical and contractile activity by activating $A_1$ receptors. Combined with coronary vasodilatation mediated via $A_2$ receptors, adenosine has a negative chronotropic, inotropic, dromotropic, bathmotropic and bradycardiac effect and reduces the volume of the heart per minute.

Adenosine $A_1$ receptor antagonists or adenosine $A_3$ receptor antagonists can prevent the damage caused to the heart and brain or lungs by ischaemia and subsequent reperfusion. As a result, adenosine antagonists can be used for the prevention or early treatment of damage to the heart caused by ischaemia/reperfusion e.g. after coronary bypass surgery, heart transplants, angioplasty or thrombolytic therapy of the heart and similar interventions. Moreover, adenosine antagonists can be used for the early treatment of cerebral ischaemia. The same is true of the lungs.

On the kidneys, the activation of $A_1$ receptors causes vasoconstriction of afferent arterioles and as a result a drop in renal bloodflow and glomerular filtration. $A_1$ antagonists act on the kidneys as powerful potassium-saving diuretics and can thus be used to protect the kidneys and to treat oedema, renal insufficiency and acute kidney failure.

On account of the adenosine antagonism on the heart and the diuretic effect, $A_1$ antagonists can be used to therapeutic effect in various cardiovascular diseases, e.g. in cardiac insufficiency, arrythmias (bradyarrythmias) associated with hypoxia or ischaemia, transmission disorders, hypertension, ascites in liver failure (hepato-renal syndrome) and as an analgesic in circulatory disorders.

Adenosine may stimulate or inhibit cell apoptosis, via the adenosine $A_3$ receptors and depending on the type of cell and the concentration of the receptor ligand. This effect can be reversed by adenosine $A_3$ receptor antagonists. Consequently, adenosine $A_3$ receptor antagonists are possible therapeutic agents for diseases in which a disruption of apoptosis is involved, such as for example inflammatory diseases such as arthritis, autoimmune diseases such as lupus erythematodes disseminatus or scleroderma and cancer. Types of cancer which overexpress the adenosine receptor would be particularly suitable for treatment with adenosine $A_3$ receptor antagonists. Moreover, adenosine $A_3$ receptor antagonists may be used to promote the immunological protective mechanisms against any remaining malignant cancer cells (e.g. after surgical removal of a colon carcinoma or other types of tumour).

$A_3$ antagonists inhibit the degranulation of mast cells caused by $A_3$ receptor activation and are therefore therapeutically useful in all disease and pathological situations connected with mast cell degranulation: e.g. as anti-inflammatory substances, in hypersensitivity reactions such as e.g. asthma, allergic rhinitis, urticaria, in myocardial reperfusion injury, scleroderma, arthritis, autoimmune diseases, inflammatory bowel diseases and the like.

Cystic fibrosis—also known as mucoviscidosis—is an inherited metabolic (a major metabolic) disorder caused by a genetic defect on a certain chromosome. As a result of increased production and greater viscosity of the secretions of the mucosal glands in the bronchi, it may lead to severe complications in the airways. Preliminary investigations have shown that $A_1$ antagonists increase the efflux of chloride ions, e.g. in CF PAC cells. On the basis of these findings, it may be expected that, in patients suffering from cystic fibrosis (mucoviscidosis), the compounds according to the invention will regulate the disrupted electrolyte balance of the cells and alleviate the symptoms of the disease.

DETAILED DESCRIPTION OF THE INVENTION

In its first aspect, the invention provides new imidazotriazolopyrimidine derivatives of the formula (I)

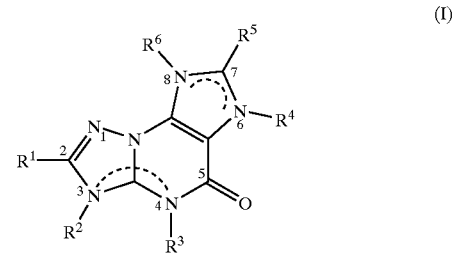

(I)

wherein the dotted lines between the nitrogen atoms of the above general formula I indicate the existence of a double bond in one of two possible positions, so that the groups $R^4$ and $R^6$ and $R^3$ and $R^2$ need not be present simultaneously and wherein:

$R^1$ denotes hydrogen, a $C_{1-8}$-alkyl, $C_{2-8}$-alkenyl or $C_{2-8}$-alkynyl group which may optionally be mono- or polysubstituted by —CN, —CH$_2$NR$^7$R$^8$, —COOR$^9$, —CONR$^7$R$^8$, —CHO, —COR$^{10}$, —CH(OH)R$^{10}$, —CH(OR$^9$)$_2$, —CH=CH—R$^{11}$, —CH=NOH, —CH=NOR$^9$, —NR$^7$R$^8$, —NHCOR$^9$, —NHCONR$^7$R$^8$, —NHCOOR$^9$, —NHCONHPhenyl, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, OCONR$^7$R$^8$, halogen, 1,3-dioxane or optionally methyl-substituted 1,3-dioxolane;

$R^1$ denotes —CHO, —COOR$^9$, —CONR$^7$R$^8$ or NR$^7$R$^8$;

$R^1$ denotes $C_{3-7}$-cycloalkyl, preferably cyclopentyl or cyclohexyl, which may optionally be substituted by =O, —OR$^9$, OCOR$^9$ or —OCOPyridyl;

$R^1$ denotes phenyl which may optionally be substituted by $C_{14}$-alkyl, preferably methyl, —CN, —COOR$^9$, NR$^7$R$^8$, —OR$^9$, —OCH$_2$COOR$^9$, —OCH$_2$CONR$^7$R$^8$, —SO$_3$H or halogen;

$R^1$ denotes phenyl-$C_{1-6}$-alkyl, preferably phenyl-$C_{1-4}$-alkyl, phenyl-$C_{2-6}$-alkenyl or phenyl-$C_{2-6}$-alkynyl, wherein the phenyl ring may optionally be substituted, either directly or via an alkylene bridge having 1 to 4 carbon atoms, by one or more of the groups $C_{1-3}$-alkyl, —CN, —CH$_2$OCOR$^9$, —COOR$^9$, —CF$_3$, —CONR$^7$R$^8$, —CH$_2$OR$^9$, —CHO, —CH=NOR$^9$, —COR$^{10}$, —CH(OH)R$^{10}$, —CH(OR$^9$)$_2$, —CH=CH—R$^{11}$, —CH$_2$—O—CONR$^7$R$^8$, —CH$_2$—CH$_2$—O—CONR$^7$R$^8$, —CO—R$^9$, —CO—C$_{1-4}$- alkyl—NR$^7$R$^8$, NR$^7$R$^8$, —NO$_2$, —NHCOR$^9$, —NHCONR$^7$R$^8$, —NHCOOR$^9$, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, —OCONR$^7$R$^8$, halogen, 1,3-dioxane or optionally methyl-substituted 1,3-dioxolane;

R$^1$ denotes C$_{3-7}$-cycloalkyl-C$_{1-6}$-alkyl, C$_{3-7}$-cycloalkyl-C$_{2-6}$-alkenyl, C$_{3-7}$-cycloalkyl-C$_{2-6}$-alkynyl, wherein the cycloalkyl group may optionally be substituted, either directly or via an alkylene bridge having 1 to 4 carbon atoms, by one or more of the groups C$_{1-3}$-alkyl, —CN, —CH$_2$OCOR$^9$, —COOR$^9$, —CF$_3$, —CONR$^7$R$^8$, —CH$_2$OR$^9$, —CHO, —CH=NOR$^9$, —COR$^{10}$, —CH(OH)R$^{10}$, —CH(OR$^9$)$_2$, —CH=CH—R$^{11}$, —CH$_2$OCONR$^7$R$^8$, —CH$_2$—CH$_2$—O—CONR$^7$R$^8$, —CO—R$^9$, —CO—C$_{1-4}$-Alkyl-NR$^7$R$^8$, NR$^7$R$^8$, —NO$_2$, —NHCOR$^9$, —NHCONR$^7$R$^8$, —NHCOOR$^9$, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, —OCONR$^7$R$^8$, halogen, optionally methyl-substituted 1,3-dioxolane or 1,3-dioxane;

R$^1$ denotes a norbornane, norbornene, C$_{3-6}$-dicycloalkyl-methyl, preferably dicyclopropylmethyl, adamantane or noradamantane group which may optionally be substituted by C$_{1-4}$-alkyl, preferably methyl;

R$^1$ denotes a group of formula A—C$_{1-6}$-alkyl, A—CONH—C$_{1-6}$-alkyl, A—CONH—C$_{2-6}$-alkenyl, A—CONH—C$_{2-6}$-alkynyl, A—NH—CO—C$_{1-6}$-alkyl, A—NH—CO—C$_{2-6}$-alkenyl, A—NH—CO—C$_{2-6}$-alkynyl, A—C$_{2-6}$-alkenyl, A—C$_{2-6}$-alkynyl or A—, where A is a C- or N-linked 5-, 6- or 7-membered heterocycle, which contains one or more heteroatoms selected from the group comprising nitrogen, oxygen or sulphur and may optionally be mono- or polysubstituted, preferably monosubstituted, by benzyl, optionally methoxy-substituted benzyl, C$_{1-4}$-alkyl, —CN, —CH$_2$NR$^7$R$^8$, —COOR$^9$, —CONR$^7$R$^8$, —COR$^{10}$, —NO$_2$, —NH$_2$, —OR$^9$, =O, a ketal, ethyleneketal, —SO$_3$H, —SO$_2$—R$^9$ or halogen;

R$^2$ or R$^3$ denotes a C$_{1-8}$-alkyl, C$_{2-8}$-alkenyl or C$_{2-8}$-alkynyl group which may optionally be mono- or polysubstituted by —CN, —CH$_2$NR$^7$R$^8$, —COOR$^9$, —CONR$^7$R$^8$, —CHO, —COR$^{10}$, —CH(OH)R$^{10}$, —CH(OR$^9$)$_2$, —CH=CH—R$^{11}$, —CH=NOH, —CH=NOR$^9$, —NR$^7$R$^8$, —NHCOR$^9$, —NHCONR$^7$R$^8$, —NHCOOR$^9$, —NHCONHPhenyl, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, OCONR$^7$R$^8$, halogen, 1,3-dioxane or optionally methyl-substituted 1,3-dioxolane;

R$^2$ or R$^3$ denotes phenyl-C$_{1-6}$-alkyl, preferably phenyl-C$_{1-4}$-alkyl, phenyl-C$_{2-6}$-alkenyl or phenyl-C$_{2-6}$-alkynyl, wherein the phenyl ring may optionally be substituted, either directly or via an alkylene bridge having 1 to 4 carbon atoms, by one or more of the groups C$_{1-3}$-alkyl, —CN, —CH$_2$OCOR$^9$, —COOR$^9$, —CF$_3$, —CONR$^7$R$^8$, —CH$_2$OR$^9$, —CHO, —CH=NOR$^9$, —COR$^{10}$, —CH(OH)R$^{10}$, CH(OR$^9$)$_2$, —CH=CH—R$^{11}$, —CH$_2$—O—CONR$^7$R$^8$, —CH$_2$—CH$_2$—O—CONR$^7$R$^8$, —CO—R$^9$, —CO—C$_{1-4}$-alkyl-NR$^7$R$^8$, NR$^7$R$^8$, —NO$_2$, —NHCOR$^9$, —NHCONR$^7$R$^8$, —NHCOOR$^9$, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, —OCONR$^7$R$^8$, halogen, 1,3-dioxane or optionally methyl-substituted 1,3-dioxolane;

R$^2$ or R$^3$ denotes a group of formula A—C$_{1-6}$-alkyl, A—CONH—C$_{1-6}$-alkyl, A—CONH—C$_{2-6}$-alkenyl, A—CONH—C$_{2-6}$-alkynyl, A—NH—CO—C$_{1-6}$-alkyl, A—NH—CO—C$_{2-6}$-alkenyl, A—NH—CO—C$_{2-6}$-alkynyl, A—C$_{2-6}$-alkenyl, A—C$_{2-6}$-alkynyl or A—, where A is a C- or N-linked 5-, 6- or 7-membered heterocycle, which contains one or more heteroatoms selected from the group comprising nitrogen, oxygen or sulphur and may optionally be mono- or polysubstituted, preferably monosubstituted, by benzyl, optionally methoxy-substituted benzyl, C$_{1-4}$-alkyl, —CN, —CH$_2$NR$^7$R$^8$, —COOR$^9$, —CONR$^7$R$^8$, —COR$^{10}$, —NO$_2$, —NH$_2$, —OR$^9$, =O, a ketal, ethyleneketal, —SO$_3$H, —SO$_2$—R$^9$ or halogen;

R$^4$ or R$^5$ denotes hydrogen, C$_{1-4}$-alkyl which may optionally be substituted by —NR$^7$R$^8$, benzyl, but preferably hydrogen;

R$^5$ denotes hydrogen, a C$_{1-8}$-alkyl, C$_{2-8}$-alkenyl or C$_{2-8}$-alkynyl group which may optionally be mono- or polysubstituted by —CN, —CH$_2$NR$^7$R$^8$, COOR$^9$, —CONR$^7$R$^8$, —CHO, —COR$^{10}$, —CH(OH)R$^{10}$, —CH(OR$^9$)$_2$, —CH=CH—R$^{11}$, —CH=NOH, —CH=NOR$^9$, —NR$^7$R$^8$, —NHCOR$^9$, —NHCONR$^7$R$^8$, —NHCOOR$^9$, —NHCONHPhenyl, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, OCONR$^7$R$^8$, halogen, 1,3-dioxane or optionally methyl-substituted 1,3-dioxolane;

R$^5$ denotes C$_{3-7}$-cycloalkyl, preferably cyclopentyl or cyclohexyl, which may optionally be substituted by =O, —OH, —OR$^9$, OCOR$^9$ or —OCOPyridyl;

R$^5$ denotes phenyl which may optionally be substituted by —OH, halogen, —OR$^9$, C$_{1-4}$-alkyl, preferably —CH$_3$, —NH$_2$, —COOH, —SO$_3$H, —COOR$^9$, —OCH$_2$COOR$^9$, —CN or —OCH$_2$CONR$^7$R$^8$;

R$^5$ denotes phenyl-C$_{1-6}$-alkyl, preferably phenyl-C$_{1-4}$-alkyl, phenyl-C$_{2-6}$-alkenyl or phenyl-C$_{2-6}$-alkynyl, wherein the phenyl ring may optionally be substituted, either directly or via an alkylene bridge having 1 to 4 carbon atoms, by one or more of the groups C$_{1-3}$-alkyl, —CN, —CH$_2$OCOR$^9$, —COOR$^9$, —CF$_3$, —CONR$^7$R$^8$, —CH$_2$OR$^9$, —CHO, —CH=NOR$^9$, —COR$^{10}$, —CH(OH)R$^{10}$, —CH(OR$^9$)$_2$, —CH=CH—R$^{11}$, —CH$_2$—O—CONR$^7$R$^8$, —CH$_2$—CH$_2$—O—CONR$^7$R$^8$, —CO—R$^9$, —CO—C$_{1-4}$-alkyl-NR$^7$R$^8$, NR$^7$R$^8$, —NO$_2$, —NHCOR$^9$, —NHCONR$^7$R$^8$, —NHCOOR$^9$, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, —OCONR$^7$R$^8$, halogen, 1,3-dioxane or optionally methyl-substituted 1,3-dioxolane;

R$^5$ denotes a norbornane, norbornene, C$_{3-6}$-dicycloalkyl-methyl, preferably dicyclopropylmethyl, adamantane or noradamantane group which may optionally be substituted by C$_{1-4}$-alkyl, preferably methyl;

R$^5$ denotes —CHO, —COOR$^9$, —CONR$^7$R$^8$ or NR$^7$R$^8$;

R$^5$ denotes C$_{3-7}$-cycloalkyl-C$_{1-6}$-alkyl, C$_{3-7}$-cycloalkyl-C$_{2-6}$-alkenyl, C$_{3-7}$-cycloalkyl-C$_{2-6}$-alkynyl, wherein the cycloalkyl group may optionally be substituted, either directly or via an alkylene bridge having 1 to 4 carbon atoms, by one or more of the groups $C_{1-3}$-alkyl, —CN, —CH$_2$OCOR$^9$, —COOR$^9$, —CF$_3$, —CONR$^7$R$^8$, —CH$_2$OR$^9$, —CHO, —CH=NOR$^9$, —COR$^{10}$, —CH(OH)R$^{10}$, —CH(OR$^9$)$_2$, —CH=CH—R$^{11}$, —CH$_2$—OCONR$^7$R$^8$, —CH$_2$—CH$_2$—O—CONR$^7$R$^8$, —CO—R$^9$, —CO—C$_{1-4}$-Alkyl—NR$^7$R$^8$, NR$^7$R$^8$, —NO$_2$, —NHCOR$^9$, —NHCONR$^7$R$^8$, —NHCOOR$^9$, —OR$^9$, —OCOR$^9$, —OCOPyridyl, —OCH$_2$COOR$^9$, —OCH$_2$—CONR$^7$R$^8$, —OCH$_2$—CH$_2$—NR$^7$R$^8$, —OCH$_2$CH$_2$OR$^9$, —OCH$_2$—CH$_2$OCOR$^9$, —OCONR$^7$R$^8$, halogen, 1,3-dioxane or optionally methyl-substituted 1,3-dioxolane;

$R^5$ denotes a group of formula A—C$_{1-6}$-alkyl, A—CONH—C$_{1-6}$-alkyl, A—CONH—C$_{2-6}$-alkenyl, A—CONH—C$_{2-6}$-alkynyl, A—NH—CO—C$_{1-6}$-alkyl, A—NH—CO—C$_{2-6}$-alkenyl, A—NH—CO—C$_{2-6}$-alkynyl, A—C$_{2-6}$-alkenylene, A—C$_{2-6}$-alkynylene or A—, where A is a C- or N-linked 5-, 6- or 7-membered heterocycle, which contains one or more heteroatoms selected from the group consisting of nitrogen, oxygen and sulphur and may optionally be mono- or polysubstituted, preferably monosubstituted, by benzyl, optionally methoxy-substituted benzyl, $C_{1-4}$-alkyl, —CN, —CH$_2$NR$^7$R$^8$, —COOR$^9$, —CONR$^7$R$^8$, —COR$^{10}$, —NO$_2$, —NH$_2$, —OR$^9$, =O, a ketal, ethyleneketal, —SO$_3$H, —SO$_2$—R$^9$ or halogen;

$R^7$ denotes hydrogen, $C_{1-8}$-alkyl, preferably $C_{1-4}$-alkyl, which may optionally be substituted by —COOR$^9$, —COR$^{10}$, —OR$^9$, OCOR$^9$, amino, phenyl, methoxy-substituted phenyl or amino, or a $C_{3-6}$-cycloalkyl;

$R^7$ denotes a 5-, 6- or 7-membered heterocycle C-linked directly or via a $C_{1-4}$-alkyl chain, which contains one, two or three heteroatoms selected from the group consisting of nitrogen, oxygen and sulphur and which is optionally mono- or polysubstituted, preferably monosubstituted, by benzyl, methoxy-substituted benzyl, $C_{1-4}$-alkyl, halogen, —OR$^9$, —CN, —NO$_2$, —NH$_2$, =O, —SO$_3$H or —COOR$^9$;

$R^8$ denotes hydrogen, $C_{1-8}$-alkyl, preferably $C_{1-4}$-alkyl, which may optionally be substituted by —COOR$^9$, —COR$^{10}$, —OR$^9$, OCOR$^9$, amino, phenyl, methoxy-substituted phenyl or amino, or a $C_{3-6}$-cycloalkyl, or $R^8$ denotes a 5-, 6- or 7-membered heterocycle C-linked directly or via a $C_{1-4}$-alkyl chain, which contains one, two or three heteroatoms selected from the group consisting of nitrogen, oxygen and sulphur and which is optionally mono- or polysubstituted, preferably monosubstituted, by benzyl, methoxy-substituted benzyl, $C_{1-4}$-alkyl, halogen, —OR$^9$, —CN, —NO$_2$, —NH$_2$, =O, —SO$_3$H or —COOR$^9$; or $R^7$ and $R^8$ together with the nitrogen atom form a saturated or unsaturated 5- or 6-membered ring which may contain nitrogen, oxygen or sulphur as further heteroatoms, whilst the heterocycle may be substituted by a branched or unbranched alkyl group having 1 to 4 carbon atoms, preferably methyl, or may carry one of the groups —CN, —COOR$^9$, —CONH$_2$, —NO$_2$, —NH$_2$, —OR$^9$, —SO$_3$H, —SO$_2$—R$^9$, halogen or —(CH$_2$)$_n$-phenyl, —(CH$_2$)$_n$—NH$_2$, =O, —OCH$_2$—CH$_2$—O—, —OCH$_2$—CH$_2$—CH$_2$—O—, —(CH$_2$)$_n$—NH—C$_{1-4}$-alkyl, —(CH$_2$)$_n$—N(C$_{1-4}$-alkyl)$_2$, —(CH$_2$)$_n$—NHCOOR$^9$, wherein n=1, 2, 3 or 4;

$R^9$ denotes hydrogen, $C_{1-4}$-alkyl, $C_{2-4}$-alkenyl, $C_{2-4}$-alkynyl, a benzyl or phenyl group which may optionally be mono- or polysubstituted by —OCH$_3$;

$R^{10}$ denotes $C_{1-4}$-alkyl, $C_{2-4}$-alkenyl, $C_{2-4}$-alkynyl, optionally methoxy-substituted phenyl, optionally methoxy-substituted benzyl, $C_{3-6}$-cycloalkyl;

$R^{11}$ denotes hydrogen, $C_{1-3}$-alkyl, —COOR$^9$, —CH$_2$OR$^9$, —CH$_2$NR$^7$R$^8$, —CONR$^7$R$^8$ or optionally methoxy-substituted phenyl, optionally in the form of their racemates, their enantiomers, their diastereomers and mixtures thereof, and optionally the pharmacologically acceptable acid addition salts thereof.

These are adenosine antagonists and are useful for, inter alia, the treatment of senile dementia of the Alzheimer's type.

Preferred compounds of general formula (I) are those wherein $R^1$ denotes hydrogen, $C_{1-8}$-alkyl which may optionally be substituted by —COOH, —COO—C$_{1-4}$-alkyl, —COO-phenyl, —COO-benzyl, —CONR$^7$R$^8$, —CO—C$_{1-4}$-alkyl-NR$^7$R$^8$, —CO—C$_{1-4}$-alkyl, —CHO, —NR$^7$R$^8$, =NOH, —NHCO—C$_{1-4}$-alkyl, —NHCO-phenyl, hydroxy, =O, $C_{1-4}$-alkoxy, phenyloxy, —O-phenyl-C$_{1-4}$-alkyloxy, benzyloxy, —O-benzyl—O—C$_{1-4}$-alkyloxy, —OCO—C$_{1-4}$-alkyl, —OCO-phenyl, —OCO-benzyl, —OCO-pyridyl, —O—C$_{2-4}$-alkylene or halogen;

$R^1$ denotes —CHO, —COOH, —COO—C$_{1-4}$-alkyl, —COO-phenyl, —COO-benzyl, —CONR$^7$R$^8$ or an amine of general formula NR$^7$R$^8$;

$R^1$ denotes phenyl which may optionally be substituted by $C_{1-4}$-alkyl, -CO—C$_{1-4}$-alkyl, $C_{1-4}$-alkyl-NR$^7$R$^8$, $C_{1-4}$-alkyl-OH, $C_{1-4}$-alkyl=NOH, —COOH, —COO—C$_{1-4}$-alkyl, —COO—phenyl, —COO-benzyl, —CONR$^7$R$^8$, —CO—C$_{1-4}$-alkyl—NH$_2$, NR$^7$R$^8$, hydroxy, $C_{1-4}$-alkyloxy, benzyloxy, phenyloxy, —OCO—C$_{1-4}$-alkyl, —OCO-phenyl, —OCO-benzyl, —OCO-pyridyl, —O—C$_{2-4}$-alkenyl or halogen, preferably chlorine or fluorine;

$R^1$ denotes a $C_{3-6}$-cycloalkyl or $C_{3-6}$-cycloalkyl-C$_{1-4}$-alkyl group which may optionally be substituted by =O, hydroxy, $C_{1-4}$-alkyl or $C_{1-4}$-alkyloxy;

$R^1$ denotes a norbornane, norbornene, adamantane or noradamantane group which may optionally be substituted by $C_{1-4}$-alkyl, preferably methyl;

$R^1$ denotes phenyl-C$_{1-4}$-alkyl, preferably benzyl, phenyl-C$_{2-6}$-alkenyl or phenyl-C$_{2-6}$-alkynyl, wherein the phenyl ring may optionally be substituted by $C_{1-4}$-alkyl, —CO—C$_{1-4}$-alkyl, $C_{1-4}$-alkyl-NR$^7$R$^8$, $C_{1-4}$-alkyl-OH, $C_{1-4}$-alkyl=NOH, —COOH, —COO—C$_{1-4}$-alkyl, —COO-phenyl, —COO-benzyl, —CONR$^7$R$^8$, —CO—C$_{1-4}$-alkyl-NH$_2$, NR$^7$R$^8$, hydroxy, $C_{1-4}$-alkyloxy, benzyloxy, phenyloxy, —OCO—C$_{1-4}$-alkyl, —OCO-phenyl, —OCO-benzyl, —OCO-pyridyl, —O—C$_{2-4}$-alkylene or halogen, preferably chlorine or fluorine;

$R^1$ denotes a 5- or 6-membered heterocycle optionally C- or N-linked either directly or via an alkylene bridge having 1 to 4 carbon atoms, which contains one, two or three heteroatoms selected from the group comprising nitrogen or oxygen and which is optionally mono- or polysubstituted by benzyl or $C_{1-4}$-alkyl;

$R^2$ or $R^3$ denotes a $C_{1-8}$-alkyl which may optionally be substituted by —NR$^7$R$^8$, OH or COOH; or $R^2$ or $R^3$ denotes $C_{2-8}$-alkenyl, phenyl-C$_{1-4}$-alkyl, preferably benzyl, phenyl-C$_{2-6}$-alkenyl or phenyl-C$_{2-6}$-alkynyl, whilst the phenyl ring may optionally be substituted by hydroxy, $C_{1-4}$-alkyl, $C_{1-4}$-alkyloxy, —NR$^7$R$^8$ or halogen, preferably chlorine or fluorine;

$R^2$ or $R^3$ denotes a 5- or 6-membered heterocycle optionally C- or N-linked either directly or via an alkylene bridge having 1 to 4 carbon atoms, which contains one, two or three heteroatoms selected from the group comprising nitrogen or oxygen and which is optionally mono- or polysubstituted by benzyl or $C_{1-4}$-alkyl;

$R^4$ or $R^6$ denotes hydrogen, $C_{1-4}$-alkyl which may optionally be substituted by —$NR^7R^8$, or benzyl;

$R^5$ denotes hydrogen, $C_{1-8}$-alkyl, preferably $C_{1-6}$-alkyl;

$R^5$ denotes phenyl which may optionally be substituted by $C_{1-4}$-alkyl, $C_{1-4}$-alkyloxy, hydroxy, —$NR^7R^8$ or halogen, preferably chlorine or fluorine;

$R^5$ denotes phenyl-$C_{1-6}$-alkyl, preferably benzyl, whilst the phenyl ring may optionally be substituted by $C_{1-4}$-alkyl, $C_{1-4}$-alkyloxy, hydroxy, —$NR^7R^8$ or halogen, preferably chlorine or fluorine;

$R^5$ denotes an optionally substituted amine, preferably —$NR^7R^8$;

$R^5$ denotes a 5- or 6-membered heterocycle optionally C- or N-linked either directly or via a $C_{1-4}$-alkylene bridge, which contains one or more heteroatoms selected from the group comprising nitrogen or oxygen and which is optionally substituted by benzyl or $C_{1-4}$-alkyl;

$R^5$ denotes a $C_{3-6}$-cycloalkyl which may optionally be substituted by =O, hydroxy, $C_{1-4}$-alkyl or $C_{1-4}$-alkyloxy;

$R^5$ denotes a norbornane, norbornene, adamantane or noradamantane group which may optionally be substituted by $C_{1-4}$-alkyl, preferably methyl;

$R^7$ denotes hydrogen, a branched or unbranched $C_{1-4}$-alkyl group;

$R^7$ denotes a C-linked 5- or 6-membered heterocycle which contains one, two or three heteroatoms selected from the group consisting of nitrogen, oxygen and sulphur and which is optionally substituted by benzyl, $C_{1-4}$-alkyl, $C_{1-4}$-alkyloxy, halogen, —CN, —$NO_2$, —$NH_2$, —OH or =O;

$R^8$ denotes hydrogen, a branched or unbranched $C_{1-4}$-alkyl group;

$R^8$ denotes a C-linked 5- or 6-membered heterocycle which contains one, two or three heteroatoms selected from the group consisting of nitrogen, oxygen and sulphur and which is optionally substituted by benzyl, $C_{1-4}$-alkyl, $C_{1-4}$-alkyloxy, halogen, —CN, —$NO_2$, —$NH_2$, —OH or =O; or $R^7$ and $R^8$ together with the nitrogen atom form a saturated or unsaturated 5- or 6-membered ring which may contain nitrogen or oxygen as further heteroatoms, whilst the heterocycle may be substituted by a branched or unbranched alkyl group having 1 to 4 carbon atoms, preferably methyl, or by a —$(CH_2)_{1-4}$-phenyl group, preferably benzyl, optionally in the form of their racemates, their enantiomers, their diastereomers and mixtures thereof, and optionally the pharmacologically acceptable acid addition salts thereof.

Also preferred are the compounds of general formula (I) wherein $R^1$ denotes hydrogen, $C_{1-6}$-alkyl, preferably $C_{1-4}$-alkyl, which may optionally be substituted by —CO—$C_{1-4}$-alkyl, —CHO, —COOH, —COO—$C_{1-4}$-alkyl, —COO-phenyl, —COO-benzyl, —$CONR^7R^8$, —CO—$C_{1-4}$-alkyl-$NR^7R^8$, —$NR^7R^8$, —NHCO—$C_{1-4}$-alkyl, —NHCO-Phenyl, hydroxy, =O, $C_{1-4}$-alkoxy, phenyloxy, —O-phenyl—O—$C_{1-4}$-alkyloxy, benzyloxy, —O-benzyl—O—$C_{1-4}$-alkyloxy, —OCO—$C_{1-4}$-alkyl, —OCO-phenyl, —OCO-pyridyl, —OCO-benzyl, —O—$C_{2-4}$-alkylene or halogen;

$R^1$ denotes phenyl, whilst the phenyl ring may optionally be substituted by $C_{1-4}$-alkyl, hydroxy, $C_{1-4}$-alkyloxy, $NR^7R^8$, halogen, preferably fluorine or chlorine;

$R^1$ denotes phenyl-$C_{1-3}$-alkyl, preferably benzyl, whilst the phenyl ring may optionally be substituted by $C_{1-4}$-alkyl, —CO—$C_{1-4}$-alkyl, —$C_{1-4}$-alkyl-$NR^7R^8$, —$C_{1-4}$-alkyl—OH, —COOH, —COO—$C_{1-4}$-alkyl, —COO-phenyl, —COO-benzyl, —$CONR^7R^8$, —CO—$C_{1-4}$-alkyl-$NR^7R^8$, $NR^7R^8$, hydroxy, $C_{1-4}$-alkyloxy, benzyloxy, phenyloxy, —OCO—$C_{1-4}$-alkyl, —OCO-phenyl, —OCO-benzyl, —OCO-pyridyl, —O—$C_{2-4}$-alkylene or halogen, preferably fluorine or chlorine;

$R^1$ denotes a cyclopentyl, cyclohexyl, cyclopentanone, cyclohexanone, hydroxycyclopentane or hydroxycyclohexane linked via a single bond or via an alkylene chain having 1 to 4 carbon atoms;

$R^1$ denotes —CHO, —COOH, —COO—$C_{1-4}$-alkyl, —COO-phenyl, —COO-benzyl, —CO—NH—$C_{1-4}$-alkyl, —CO—N($C_{1-4}$-alkyl)$_2$ or —CO—NH-phenyl;

$R^1$ denotes an amine of general formula $NR^7R^8$;

$R^1$ denotes a heterocycle selected from the group consisting of furan, tetrahydrofuran, α-pyran, γ-pyran, dioxolane, tetrahydropyran, dioxane, thiophene, thiolane, dithiolane, pyrrole, pyrroline, pyrrolidine, pyrazole, pyrazoline, imidazole, imidazoline, imidazolidine, triazole, pyridine, piperidine, pyridazine, pyrimidine, pyrazine, piperazine, triazine, morpholine, thiomorpholine, oxazole, isoxazole, oxazine, thiazole, isothiazole, thiadiazole, oxadiazole and pyrazolidine linked via a single bond or via an alkylene chain with 1 to 4 carbon atoms;

$R^2$ or $R^3$ denotes $C_{1-7}$-alkyl, preferably $C_{1-5}$-alkyl, which may optionally be substituted by —$NR^7R^8$, OH or COOH; or $R^2$ or $R^3$ denotes $C_{2-5}$-alkenyl or phenyl-$C_{1-3}$-alkyl, preferably benzyl, whilst the phenyl ring may be substituted by $C_{1-4}$-alkyl, —$NR^7R^8$, hydroxy, $C_{1-4}$-alkyloxy or halogen, preferably chlorine or fluorine;

$R^2$ or $R^3$ denotes a heterocycle selected from the group consisting of furan, tetrahydrofuran, α-pyran, γ-pyran, dioxolane, tetrahydropyran, dioxane, thiophene, thiolane, dithiolane, pyrrole, pyrroline, pyrrolidine, pyrazole, pyrazoline, imidazole, imidazoline, imidazolidine, triazole, pyridine, piperidine, pyridazine, pyrimidine, pyrazine, piperazine, triazine, morpholine, thiomorpholine, oxazole, isoxazole, oxazine, thiazole, isothiazole, thiadiazole, oxadiazole and pyrazolidine linked via a single bond or via an alkylene chain with 1 to 4 carbon atoms;

$R^4$ or $R^6$ denotes hydrogen, $C_{1-4}$-alkyl, preferably $C_{1-3}$-alkyl, $C_{1-3}$-alkyl-$NR^7R^8$ or benzyl;

$R^5$ denotes hydrogen, $C_{1-6}$-alkyl, preferably $C_{1-4}$-alkyl;

$R^5$ denotes cyclopentyl, cyclohexyl, cyclopentanone, cyclohexanone, hydroxycyclopentane or hydroxycyclohexane;

$R^5$ denotes pyridyl, tetrahydrofuranyl, tetrahydropyranyl, furyl, morpholine, piperidine or piperazine which is optionally substituted by $C_{1-4}$-alkyl or benzyl;

$R^5$ denotes a phenyl group which may optionally be substituted by $C_{1-4}$-alkyl, halogen or hydroxy;

$R^5$ denotes phenyl-$C_{1-4}$-alkyl, preferably benzyl, whilst the phenyl ring may optionally be substituted by $C_{1-4}$- alkyl, —NR$^7$R$^8$, hydroxy, C$_{1-4}$-alkyloxy or halogen, preferably fluorine or chlorine;

R$^5$ denotes an amine of general formula —NR$^7$R$^8$;

R$^5$ denotes a norbornene, norbornane, adamantane or noradamantane group which may optionally be substituted by C$_{1-4}$-alkyl, preferably methyl;

R$^7$ denotes hydrogen, a branched or unbranched C$_{1-4}$-alkyl group;

R$^7$ denotes a C-linked heterocycle selected from the group consisting of pyrrole, pyrrolidine, pyrazole, imidazole, imidazolidine, triazole, pyridine, piperidine, pyrimidine, pyrazine, piperazine, morpholine, oxazole, isoxazole, thiazole, isothiazole and thiadiazole which is optionally substituted by C$_{1-4}$-alkyl, —NO$_2$, —NH$_2$, hydroxy, C$_{1-4}$-alkyloxy, chlorine or bromine;

R$^8$ denotes hydrogen, a branched or unbranched C$_{1-4}$-alkyl group, or

R denotes a C-linked heterocycle selected from the group consisiting of pyrrole, pyrrolidine, pyrazole, imidazole, imidazolidine, triazole, pyridine, piperidine, pyrimidine, pyrazine, piperazine, morpholine, oxazole, isoxazole, thiazole, isothiazole and thiadiazole which is optionally substituted by C$_{1-4}$-alkyl, —NO$_2$, —NH$_2$, hydroxy, C$_{1-4}$-alkyloxy, chlorine or bromine; or R$^7$ and R$^8$ together with the nitrogen atom form a saturated or unsaturated 5- or 6-membered ring which may contain nitrogen or oxygen as further heteroatoms, whilst the heterocycle may be substituted by a branched or unbranched alkyl group having 1 to 4 carbon atoms, preferably methyl, or by a —(CH$_2$)$_{1-4}$-phenyl group, preferably benzyl, optionally in the form of their racemates, their enantiomers, their diastereomers and mixtures thereof, and optionally the pharmacologically acceptable acid addition salts thereof.

Preferred compounds according to the invention are compounds of general formula (I) wherein R$^1$ denotes hydrogen, or C$_{1-4}$-alkyl, which is optionally substituted by —NHCO—C$_{1-4}$-alkyl, —NR$^7$R$^8$, hydroxy, C$_{1-4}$-alkyloxy, chlorine or bromine; or R$^1$ denotes —CHO, —COOH, —COO—C$_{1-4}$-alkyl or phenyl; or R$^1$ denotes phenyl-C$_{1-3}$-alkyl, preferably benzyl which may optionally be substituted by C$_{1-4}$-alkyl, C$_{1-4}$-alkyl-NR$^7$R$^8$, hydroxy, benzyloxy or fluorine; or R$^1$ denotes phenyloxy-C$_{1-3}$-alkyl, preferably phenyloxymethyl, which may optionally be substituted by methoxy; or R$^1$ denotes benzyloxy-C$_{1-3}$-alkyl, preferably benzyloxymethyl which may optionally be substituted by methoxy; or R$^1$ denotes benzyloxybenzyl, benzoyloxymethyl, pyridylcarbonyloxymethyl, cyclohexylmethyl, pyridylmethyl, N-pyrrolylmethyl, N-morpholinomethyl, cyclopentyl or furyl;

R$^2$ or R$^3$ denote C$_{1-5}$-alkyl, C$_{2-4}$-alkenyl or benzyl;

R$^4$ or R$^6$ denote hydrogen, C$_{1-3}$-alkyl, C$_{1-3}$-alkyl—NR$^7$R$^8$, N-morpholinoethyl or benzyl;

R$^5$ denotes hydrogen, C$_{1-4}$-alkyl, phenyl or benzyl wherein the phenyl ring may optionally be substituted by fluorine; or R$^5$ denotes pyridyl, piperidinyl, morpholinyl, piperazinyl, 4-benzylpiperazinyl, furyl, tetrahydrofuranyl, tetrahydropyranyl, NR$^7$R$^8$, cyclopentyl, cyclohexyl, adamantyl, noradamantyl, norbornyl or norbornenyl;

R$^7$ denotes hydrogen, C$_{1-4}$-alkyl or pyridyl;

R$^8$ denotes hydrogen, C$_{1-4}$-alkyl or pyridyl optionally in the form of their racemates, their enantiomers, their diastereomers and mixtures thereof, and optionally the pharmacologically acceptable acid addition salts thereof.

Also preferred according to the invention are compounds of general formula (I) wherein R$^1$ denotes hydrogen, methyl, which may optionally be substituted by —NH$_2$, —NHMe, —NMe$_2$, —N(propyl)$_2$, —NHAcetyl, hydroxy, methoxy, ethoxy, phenyloxy, methoxyphenyloxy, methoxybenzyloxy, piperazine, methylpiperazine, morpholine, benzoyloxy, pyridylcarbonyloxy, pyridine, pyridylamino, pyrrole or bromine; or R$^1$ denotes ethyl which is optionally substituted by —NH$_2$ or hydroxy; or R$^1$ denotes benzyl which is optionally substituted by hydroxy, methoxy, benzyloxy, dimethylaminoethoxy, N-morpholinoethoxy or fluorine; or R$^1$ denotes n-propyl, isopropyl, n-butyl, tert.butyl, cyclopentyl, cyclohexylmethyl, phenyl, phenylethyl, —CHO, —COOH, —COOMe, COOEt, COOPropyl, COOButyl or furan;

R$^2$ or R$^3$ denote methyl, ethyl, n-propyl, isopropyl, n-butyl, isobutyl, tert.butyl, allyl, butenyl, n-pentyl, propargyl or benzyl;

R$^4$ or R$^6$ denote hydrogen, methyl, n-propyl or benzyl; or

R$^4$ or R5 denote ethyl which is optionally substituted by morpholine;

R$^5$ denotes hydrogen, methyl, ethyl, n-propyl, isopropyl, n-butyl, tert.butyl, phenyl, benzyl, pyridyl, —NH$_2$, —NHMe, —NMe$_2$, piperidinyl, morpholinyl; or R$^5$ denotes piperazinyl which is optionally substituted by methyl or benzyl; or R$^5$ denotes furyl, tetrahydrofuranyl, tetrahydropyranyl, cyclopentyl, cyclohexyl, adamantyl, noradamantyl, norbornanyl or norbornenyl, optionally in the form of their racemates, their enantiomers, their diastereomers and mixtures thereof, and optionally the pharmacologically acceptable acid addition salts thereof.

Particularly preferred according to the invention are compounds of general formula (I) wherein R$^1$ denotes hydrogen, methyl which is optionally substituted by —NMe$_2$, hydroxy, methoxy, ethoxy, phenyloxy, methoxyphenyloxy, methoxybenzyloxy, morpholine, benzoyloxy, pyridylcarbonyloxy, pyridine, pyridylamino or pyrrole; or R$^1$ denotes ethyl, n-propyl, isopropyl, n-butyl, tert.butyl, cyclopentyl, cyclohexylmetyl or benzyl which is optionally be substituted by hydroxy, methoxy, dimethylaminoethoxy or fluorine;

phenyl, phenylethyl, —COOH, —COOMe or furan;

R$^2$ or R$^3$ denote methyl, ethyl, n-propyl, isopropyl, n-butyl, isobutyl, tert.butyl, n-pentyl, allyl, butenyl, propargyl or benzyl;

R$^4$ or R$^6$ denote hydrogen;

R$^1$ denotes hydrogen, ethyl, n-propyl, isopropyl, n-butyl, tert.butyl, phenyl, benzyl, pyridine, piperidine, morpholine, piperazine, 4-benzylpiperazinyl, tetrahydrofuranyl, tetrahydropyranyl, —NMe$_2$, cyclopentyl, cyclohexyl, adamantyl, noradamantyl, norbornanyl or 5-norbornenyl, optionally in the form of their racemates, their enantiomers, their diastereomers and mixtures thereof, and optionally the pharmacologically acceptable acid addition salts thereof.

13

Especially preferred according to the invention are compounds of general formula (I) wherein

- $R^1$ denotes methyl, which s optionally substituted by —$NH_2$, —NHMe, —N(iso-propyl)$_2$, -NHAcetyl, hydroxy, phenyloxy, methylpiperazine or pyrrole; or
- $R^1$ denotes ethyl which is optionally substituted by —$NH_2$ or hydroxy; or
- $R^1$ denotes benzyl which is optionally substituted by hydroxy, methoxy, benzyloxy, dimethylaminoethoxy, N-morpholinoethoxy or fluorine; or
- $R^1$ denotes cyclopentyl phenylethyl, —COOH, —COOPropyl, —COOButyl or furan;
- $R^2$ or $R^3$ denote ethyl, n-propyl, isopropyl, n-butyl, isobutyl, n-pentyl, allyl, butenyl or propargyl;
- $R^4$ or $R^6$ denote hydrogen, methyl or ethyl, which is substituted by morpholine;
- $R^5$ denotes methyl, ethyl, n-propyl, tert.butyl, cyclopentyl or norbornenyl, optionally in the form of their racemates, their enantiomers, their diastereomers and mixtures thereof, and optionally the pharmacologically acceptable acid addition salts thereof.

Particularly preferred are also compounds of general formula (I) wherein

- $R^1$ denotes methyl, which is optionally substituted by phenyloxy or pyrrole; or
- $R^1$ denotes benzyl which is optionally substituted by hydroxy, methoxy, dimethylaminoethoxy or fluorine; or
- $R^1$ denotes cyclopentyl, furan or phenylethyl;
- $R^2$ or $R^3$ denote ethyl, n-propyl, allyl or propargyl;
- $R^4$ or $R^1$ denote hydrogen;
- $R^5$ denotes methyl, n-propyl, tert.butyl, cyclopentyl or norbornenyl, optionally in the form of their racemates, their enantiomers, their diastereomers and mixtures thereof, and optionally the pharmacologically acceptable acid addition salts thereof.

The compounds of general formula (I) form the following isomers:

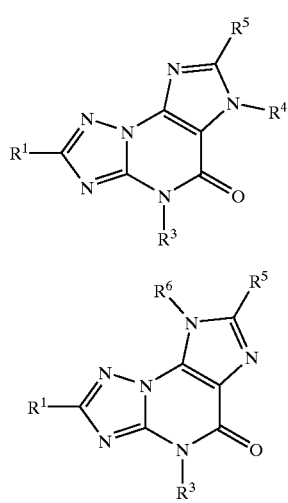

14

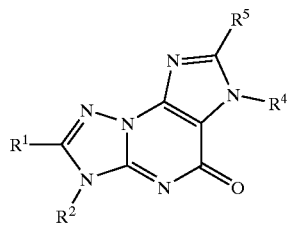

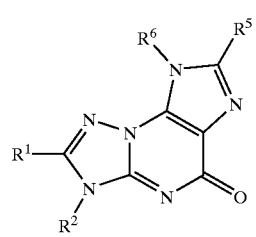

the isomers of general formulae (Ia) and (Ib) being particularly preferred, especially those wherein $R^4$ or $R^6$ are hydrogen or $C_{1-4}$-alkyl. Particularly preferred are compounds of general formula (Ia) and (Ib) wherein $R^4$ and $R^6$ denote hydrogen—in this case the isomers (Ia) and (Ib) are tautomers. According to the invention, the particularly preferred compounds are the isomers (Ia), especially those which have a I substituent in positions 2, 4 and 7.

If desired, the compounds of general formula (I) may be converted into their salts, more particularly, for pharmaceutical use, into their physiologically acceptable salts with an inorganic or organic acid. Suitable acids include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. Mixtures of the abovementioned acids may also be used.

Suitable alkyl groups (including those which are components of other groups) are branched and unbranched alkyl groups having 1 to 8 carbon atoms, preferably 1 to 4 carbon atoms, such as: methyl, ethyl, n-propyl, isopropyl, n-butyl, isobutyl, sec.butyl, tert.butyl, pentyl, isopentyl, hexyl, heptyl and octyl. In some cases the abbreviations Me, Et, n-Pr, i-Pr, n-Bu, i-Bu, t-Bu, etc. are used for the abovementioned groups.

Suitable alkenyl groups (including those which are components of other groups) are branched and unbranched alkenyl groups having 2 to 8 carbon atoms, preferably 2 to 4 carbon atoms, provided that they have at least one double bond, as well as the abovementioned alkyl groups, for example, provided that they have at least one double bond, such as vinyl (provided that no unstable enamines or enolethers are formed), propenyl, isopropenyl, butenyl, pentenyl and hexenyl.

Suitable alkynyl groups (including those which are components of other groups) are alkynyl groups having 2 to 8 carbon atoms, provided that they have at least one triple bond, such as ethynyl, propargyl, butynyl, pentynyl and hexynyl.

Suitable cycloalkyl groups having 3 to 6 carbon atoms include, for example, cyclopropyl, cyclobutyl, cyclopentyl or cyclohexyl, which may also be substituted by branched or unbranched alkyl having 1 to 4 carbon atoms, hydroxy, and/or halogen or as hereinbefore defined. Halogen generally denotes fluorine, chlorine, bromine or iodine.

Examples of N-linked cyclic groups of general formula $NR^7R^8$ include: pyrrole, pyrroline, pyrrolidine, piperidine, piperazine, morpholine, thiomorpholine, imidazole, imidazoline, imidazolidine, pyrazole, pyrazoline, pyrazolidine, preferably morpholine, piperazine and piperidine, whilst the abovementioned heterocycles may also be substituted by benzyl, alkyl having 1 to 4 carbon atoms, preferably methyl, or can be substituted as specified in the definitions.

Examples of C-linked 5- or 6-membered heterocyclic rings which may contain, nitrogen, oxygen or sulphur as heteroatoms, include, for example, furan, tetrahydrofuran, tetrahydrofuranone, -butyrolactone, -pyran, -pyran, dioxolane, tetrahydropyran, dioxane, thiophene, dihydrothiophene, thiolane, dithiolane, pyrrole, pyrroline, pyrrolidine, pyrazole, pyrazoline, imidazole, imidazoline, imidazolidine, triazole, tetrazole, pyridine, piperidine, pyridazine, pyrimidine, pyrazine, piperazine, triazine, tetrazine, morpholine, thiomorpholine, oxazole, isoxazole, oxazine, thiazole, isothiazole, thiadiazole, oxadiazole or pyrazolidine, whilst the heterocycle may be substituted as specified in the definitions.

"=O" denotes an oxygen atom linked via a double bond.

The compounds according to the invention may be prepared as described in the prior art (Tenor et al., Chem. Ber. Vol. 97 (1964) p. 1373–1382), to which reference is hereby made (diagram 1).

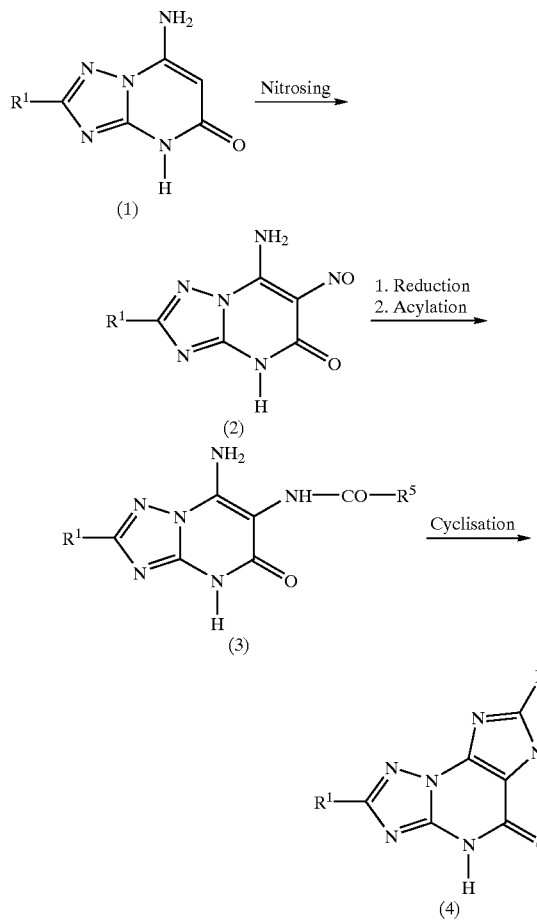

Diagram 1

The above method of synthesis already disclosed in the prior art can be used to prepare the compounds of general formula (I) according to the invention wherein the groups $R^2$ or $R^3$ and $R^4$ or $R^6$ denote hydrogen. In this case, the compounds of general formula (I) are tautomers, one tautomeric form of which is represented by formula (4) in diagram 1. The triazolopyrimidones referred to as compounds (1) in diagram 1 may be prepared by reacting cyanoacetic ester derivatives with suitably substituted 3-amino-1,2,4-triazoles as described by Tenor et al. in the introduction. The latter compounds can be obtained by methods known from the literature (*J. Org. Chem.* 1926, p. 1729; *Org. Synthesis* 26, p. 11; *J. Chem. Soc.* 1929, p. 816).

In order to obtain the compounds of general formula (I) wherein the groups $R^4$ or $R^6$ and $R^2$ or $R^3$ denote something other than hydrogen, the following procedure may be followed:

Before the reaction sequence described in the prior art and shown in diagram 1, the compounds (1) may be derivatised according to diagram 2. According to the invention, alkylation or benzylation is preferred as derivatisation.

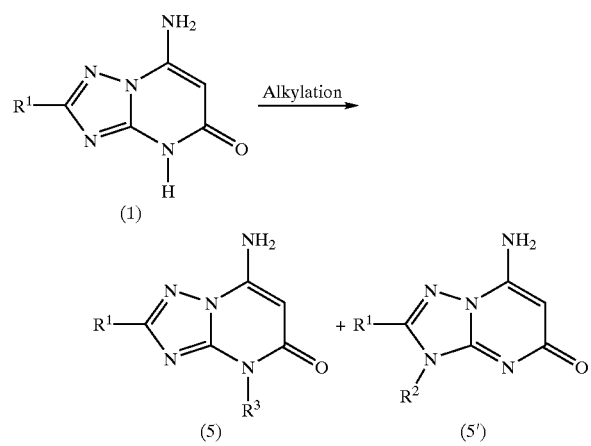

Diagram 2

The alkylation or benzylation to be carried out leads to the compounds (5). The isomeric alkylation products (5') may possibly be obtained as well. Any mixtures of products (5) and (5') obtained can be separated into the pure alkylation products (5) and (5') using purification methods known to the skilled person, such as fractional crystallisation or chromatography.

The compounds (5) and (5') are then subjected to the reaction sequence described by Tenor et al., as shown diagrammatically for the reaction of compounds (5) in diagram 3.

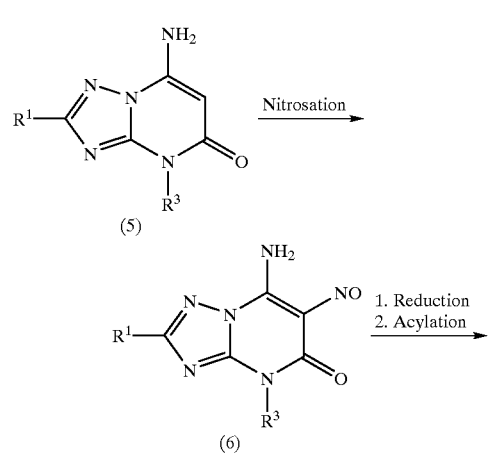

-continued

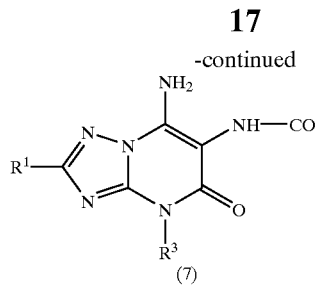
(7)

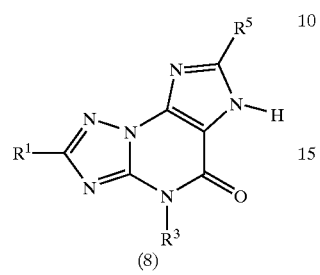
(8)

Diagram 3

The procedure described above which can be carried out analogously to the prior art can be used to prepare the compounds of general formula (I) according to the invention wherein the groups $R^4$ or $R^6$ denote hydrogen. In this case, the compounds of general formula (I) are tautomers, one tautomeric form of which is represented by formula (8) in diagram 3.

Starting from the alkylation products (5') the compounds (8') may be obtained accordingly (diagram 4).

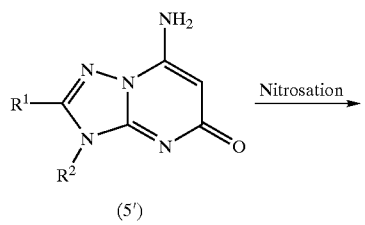
(5')

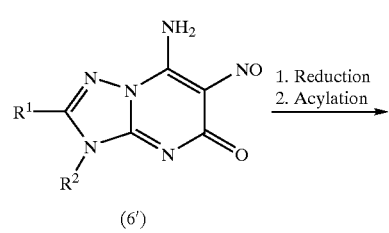
(6')

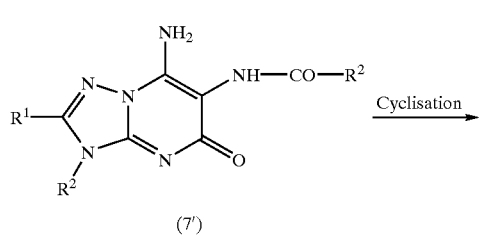
(7')

-continued

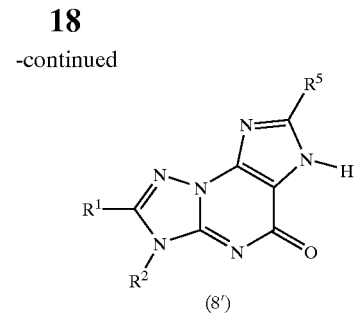
(8')

Diagram 4

The method of synthesis described above which can be carried out analogously to the prior art can be used to prepare the compounds of general formula (I) according to the invention wherein the groups $R^4$ or $R^6$ denote hydrogen. In this case, the compounds of general formula (I) are tautomers, one tautomeric form of which is represented by formula (8') in diagram 4.

Compounds (Ia) and (Ib) may be obtained by re-alkylation of the compounds (8) (Diagram 5).

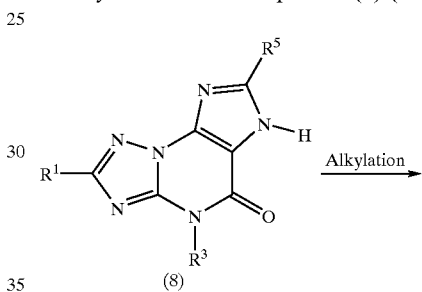
(8)

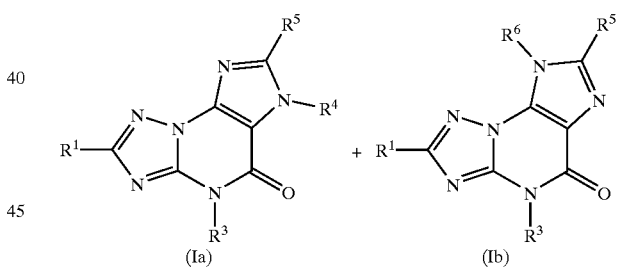
(Ia)    (Ib)

Diagram 5

Mostly the compounds (Ia) are isolated as the main products.

Analogously, the reaction of the derivatives (8') leads to the compounds (Ic) and (Id) (Diagram 6).

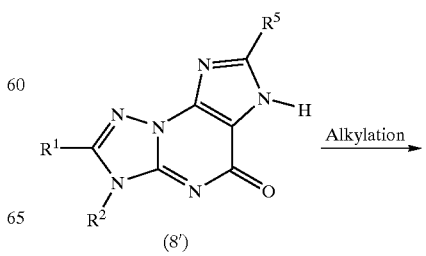
(8')

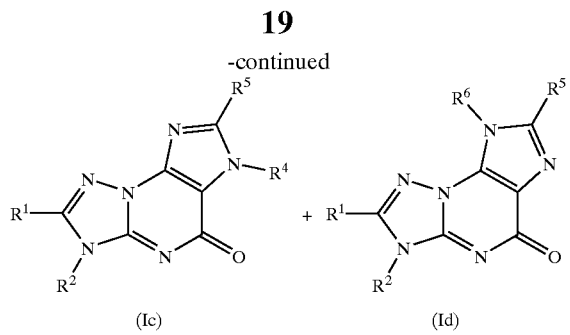

(Ic)      (Id)

Diagram 6

Mostly the compounds (Ic) are isolated as the main products.

Depending on the substitution pattern, the compounds (Ia), (Ib), (Ic) or (Id) wherein the groups $R^1$ to $R^6$ may be defined as hereinbefore, can be further functionalised using methods known from the literature. These functionalisations comprise the processes familiar to the skilled person, namely oxidation, reduction, ether splitting, acylation, alkylation, etc. Moreover, the use of common protecting groups, especially common hydroxyl and amino protecting groups may be necessary. It is particularly preferable to use the p-methoxybenzyl group as a protecting group for a hydroxyl function, for example, in conjunction with the benzyl group as an amino protecting group.

Major differences between the procedure according to the invention and the methods known from the prior art are explained in more detail in the Experimental section which follows, by means of important key stages. The Examples which follow serve to illustrate the invention without restricting its scope.

SYNTHESIS EXAMPLE I 7-cyclopentyl-4-ethyl-2-phenyloxymethyl-imidazo[4,5-e]-s-triazolo[1,5-a]pyrimidin-5-one Preliminary Stages Starting with anise alcohol and chloroacetic acid, 4-methoxybenzyloxyacetic acid may be obtained under alkaline reaction conditions. The experimental procedure for synthesising ethers in this way is known in the art and requires no detailed experimental study. Using methods known from the literature (*J. Org. Chem.* 1926, p. 1729; *Org. Synthesis* 26, p.11; *J. Chem. Soc.* 1929, p. 816) the correspondingly substituted 3-aminotriazole derivative may be obtained therefrom by reacting with aminoguanidine, and is then converted into the 7-amino-2-[(4-methoxybenzyloxy)methyl]-s-triazolo[1,5-a]pyrimidin-5-one by the method disclosed by Tenor et al. (see above).

7-amino-4-ethyl-2-[(4-methoxybenzyloxy)methyl]-s-triazolo[1,5-a]pyrimidin-5-one 145.6 g of 7-amino-2-[(4-methoxybenzyloxy)methyl]-s-triazolo[1,5-a]pyrimidin-5-one is dissolved in 1500 ml of dimethylformamide and mixed with 76.8 g of potassium carbonate. After the addition of 45.2 ml of ethyl iodide the mixture is stirred for about 1.5 days at ambient temperature. For working up, the dimethylformamide is distilled off in vacuo and the residue remaining is taken up in 500 ml of water (distilled), 500 ml of saturated NaCl solution and 1000 ml of dichloromethane. After separation of the organic phase the aqueous phase remaining is extracted three more times with 200 ml of dichloromethane. The combined organic phases are dried over magnesium sulphate and then freed from solvent. About 180 g of a solid remain, which is used in the next step without further purification.

7-amino-4-ethyl-2-[(4-methoxybenzyloxy)methyl]-6-nitroso-s-triazolo[1,5-a]pyrimidin-5-one 3.7 g of the precursor (7-amino-4-ethyl-2-[(4-methoxybenzyloxy)methyl]-s-triazolo[1,5-a]pyrimidin-5-one) are dissolved in 17 ml of dimethylformamide, and 2.69 ml of isoamyl nitrite are added whilst cooling with ice. Afterwards it is stirred at ambient temperature. After the reaction is complete (about 3 hours) 34 ml of water are added at 5–10° C. The solid obtained is separated off, washed with water and diethyl ether and recrystallised from 80 ml of ethanol. 2.0 g of 7-amino-4-ethyl-2-[(4-methoxybenzyloxy)methyl]-6-nitroso-s-triazolo[1,5-a]pyrimidin-5-one are left.

6,7-diamino-4-ethyl-2-[(4-methoxybenzyloxy)methyl]-s-triazolo[1,5-a]pyrimidin-5-one At ambient temperature, 1.5 g of 7-amino-4-ethyl-2-[(4-methoxybenzyloxy)methyl]-6-nitroso-s-triazolo[1,5-a]pyrimidin-5-one are added to 64 ml of aqueous ammonia solution (25%) and 13 ml of ethanol and dissolved therein. At 30–35° C. a solution of 3.3 g of $Na_2S_2O_4$ in 30 ml of water is added dropwise. The resulting mixture is stirred at ambient temperature until the reaction is complete (about 3–4 hours). After cooling in an ice bath, the crystals obtained are suction filtered and dried. 1.2 g of 6,7-diamino-4-ethyl-2-[(4-methoxybenzyloxy)methyl]-s-triazolo[1,5-a]pyrimidin-5-one are obtained, which is used in the next step without further purification.

7-amino-6-cyclopentylcarbonylamino-4-ethyl-2-[(4-methoxybenzyloxy)methyl]-s-triazolo[1,5-]pyrimidin-5-one 1.1 g of 6,7-diamino-4-ethyl-2-[(4-methoxybenzyloxy)methyl]-s-triazolo[1,5-a]pyrimidin-5-one are taken up in 19 ml of dimethylformamide and 0.7 g of dimethylaminopyridine (DMAP) are added. At 3–5° C. 0.5 ml of cyclopentanecarboxylic acid chloride (dissolved in 2 ml of dimethylformamide) are added with stirring. The resulting mixture is stirred for 2 hours at constant temperature. The mixture is kept at ambient temperature with stirring until the reaction is complete (about 12–16 hours). For working up, the dimethylformamide is distilled off in vacuo and the residue remaining is taken up in 20 ml of water and 20 ml of diethyl ether. The solid precipitated is separated off and washed with water and diethyl ether. After the crystals obtained (1.27 g) have been dried, the acylation product thus obtained is used in the next step without further purification.

7-cyclopentyl-4-ethyl-2-[(4-methoxybenzyloxy)methyl]-imidazo[4,5-e]-s-triazolo[1,5-a]pyrimidin-5-one 1.25 g of the acylation product synthesised earlier are taken up in 15 ml of water and 7 ml of ethanol and then 3.5 ml of an aqueous sodium hydroxide solution (50%) and 0.95 g of calcium hydroxide are added successively. The mixture thus obtained is stirred at elevated temperature (about 95° C.) until the reaction is complete (about 6 hours). For working up, it is cooled (with ice) and mixed with about 20 ml of aqueous 4N HCl solution. The solid precipitated is separated and dried. 1.1 g of 7-cyclopentyl-4-ethyl-2-[(4-methoxybenzyloxy)methyl]-imidazo[4,5-e]-s-triazolo[5-]pyrimidin-5-one is obtained, pure enough for the following reactions.

6-benzyl-7-cyclopentyl-4-ethyl-2-[(4-methoxybenzyloxy)methyl]-imidazo[4,5-e]-s-triazolo[1,5-]pyrimidin-5-one 2.11 g of 7-cyclopentyl-4-ethyl-2-[(4-methoxybenzyloxy)methyl]-imidazo[4,5-e]-s-triazolo[1,5-a]pyrimidin-5-one and 0.76 g of potassium carbonate are taken up in 50 ml of dimethylformamide. 0.65 ml of benzyl bromide are added dropwise with cooling and stirring. The solution obtained is than stirred for 2 to 3 days at ambient temperature. For working up, the dimethylformamide is distilled off in vacuo and the residue remaining is taken up in 20 ml of dichloromethane and washed with 20 ml of water. The organic phase is separated off and dried over magnesium sulphate. After the solvent has been distilled of the residue remaining is stirred in 20 ml of diethyl ether. The solid precipitated is separated and dried. 2.6 g of 6-benzyl-7-cyclopentyl-4-ethyl-2-[(4-methoxybenzyloxy)methyl]-imidazo[4,5-e]-s-triazolo[1,5-a]pyrimidin-5-one are obtained. No further purification is carried out.

6-benzyl-7-cyclopentyl-4-ethyl-2-hydroxymethyl-imidazo[4,5-e]-s-triazolo[1,5-a]pyrimidin-5-one 6-benzyl-7-cyclopentyl-4-ethyl-2-[(4-methoxybenzyloxy)methyl]-imidazo[4,5-e]-s-triazolo[1,5-a]pyrimidin-5-one (1.03 g) is dissolved in 20 ml of dichloromethane and 1.2 ml of water are added. At ambient temperature, 2,3-dichloro-5,6-dicyanobenzoquinone (DDQ, 0.68 g) is added with stirring and the mixture is stirred for a further 4 hours. After the 2,3-dichloro-5,6-dicyanobenzoquinone precipitate has been separated off, the remaining solution is washed with saturated aqueous sodium hydrogen carbonate solution and saturated aqueous sodium chloride solution and dried over sodium sulphate. The solvent is distilled of and the residue remaining is crystallised from diethyl ether. 0.74 g of 6-benzyl-7-cyclopentyl-4-ethyl-2-hydroxymethyl-imidazo[4,5-e]-s-triazolo[1,5-a]pyrimidin-5-one are obtained in the form of slightly reddish crystals which can be used in the next step without further purification.

6-benzyl-2-bromomethyl-7-cyclopentyl-4-ethyl-imidazo[4,5-e]-s-triazolo[1,5-a]pyrimidin-5-one 0.6 g of 6-benzyl-7-cyclopentyl-4-ethyl-2-hydroxymethyl-imidazo[4,5-e]-s-triazolo[1,5-a]pyrimidin-5-one are taken up in 7 ml of dichloromethane and 0.25 ml of triethylamine are added at ambient temperature with stirring. Then 0.15 ml of thionyl bromide are added. After 2 hours' stirring at constant temperature the reaction is complete. For working up, the mixture is diluted with 20 ml of dichloromethane and washed successively with 15 ml of water and 15 ml of aqueous sodium chloride solution. The organic phase is dried over magnesium sulphate and the solvent is distilled off in vacuo. The residue remaining is recrystallised from diethyl ether. 0.45 g of the title compound remain, pure enough to be used in the subsequent reactions.

6-benzyl-7-cyclopentyl-4-ethyl-2-phenyloxymethyl-imidazo[4,5-e]-s-triazolo[1,5-a]pyrimidin-5-one 66 mg of sodium hydride (66% in mineral oil) are added to a solution of 0.16 g of phenol in 15 ml of dimethylformamide. After 30 minutes' stirring at ambient temperature, 0.68 g of 6-benzyl-2-bromomethyl-7-cyclopentyl-4-ethyl-imidazo[4,5-e]-s-triazolo[1,5-a]pyrimidin-5-one are added. The mixture is stirred at elevated temperature (about 100° C.) until the reaction is complete (about 8 hours). For working up, some water is added and then the solvent is distilled off in vacuo. The residue remaining is taken up in 20 ml of dichloromethane and 20 ml of water. After acidification with aqueous 1N HCl solution, the organic phase is separated off, washed with water and dried over magnesium sulphate. The solvent is distilled off and the residue remaining is recrystallised from diethyl ether. 0.6 g of the title compound remain, pure enough to be used in the subsequent reactions.

7-cyclopentyl-4-ethyl-2-phenyloxymethyl-imidazo[4,5-e]-s-triazolo[1,5-a]pyrimidin-5-one 0.6 g of 6-benzyl-7-cyclopentyl-4-ethyl-2-phenyloxymethyl-imidazo[4,5-e]-s-triazolo[1,5-a]pyrimidin-5-one are hydrogenated in 30 ml of methanol on 0.1 g of Pearlman catalyst (60° C., 5 bar). After separation of the catalyst, the residue is evaporated to dryness. The title compound is purified by chromatography on silica gel (dichloromethane:methanol 99:1). Using the above method, 0.2 g of the title compounds were obtained (melting point 229° C.).

SYNTHESIS EXAMPLE II 7-cyclopentyl-4-ethyl-2-(methylaminomethyl)-imidazo[4,5 -e]-s-triazolo[1,5-a]pyrimid in-5-one 6-benzyl-7-cyclopentyl-4-ethyl-2-formyl-imidazo[4,5-e]-s-triazolo[1,5-a]pyrimidin-5-one 0.3 g of 6-benzyl-7-cyclopentyl-4-ethyl-2-hydroxymethyl-imidazo[4,5-e]-s-triazolo[1,5-a]pyrimidin-5-one (for preparation see Synthesis Example I) are dissolved in 1.1 ml of dichloromethane and 0.45 g of pyridinium dichromate are added. The brown suspension obtained is stirred for about 24 hours at ambient temperature. The solvent is distilled off and the residue remaining is stirred with an ethyl acetate/cyclohexane mixture (2:1.5 ml). The clear, light yellow supernatant solution is filtered through silica gel. After the solvent has been distilled off, 0.15 g of the title compound are left in the form of a colourless resin.

6-benzyl-7-cyclopentyl-4-ethyl-2-(methylaminomethyl)-imidazo[4,5-e]-s-triazolo[1,5a]pyrimidin-5-one 0.5 g of 6-benzyl-7-cyclopentyl-4-ethyl-2-formyl-imidazo[4,5-e]-s-triazolo[1,5-a]pyrimidin-5-one are hydrogenated, together with 0.1 g of methylamine, in 30 ml of methanol on 50 mg of 10% palladium on charcoal (5 bar, 20° C., 3 hours). For working up, the catalyst is filtered off and the solvent is distilled off in vacuo. The product is purified by chromatography on silica gel (dichloromethane:methanol 95:5) and yields 0.42 g of the title compound in the form of a colourless oil.

7-cyclopentyl-4-ethyl-2-(methylaminomethyl)-imidazo[4.5-e]-s-triazolo[4.5-e]1.5-a]pyrimidin-5-one 0.37 g of 2-aminomethyl-6-benzyl-7-cyclopentyl-4-ethyl-imidazo[4.5-e]-s-triazolo[1.5-a]pyrimidin-5-one are hydrogenated in 30 ml of glacial acetic acid on 50 mg of 10% palladium on charcoal (5 bar, 20° C., 19 hours). For working up, the catalyst is filtered off and the solvent is distilled off in vacuo. The crude product is purified by chromatography on silica gel (dichloromethane:methanol 90:10) and yields 0.18 g of the title compound in the form of colourless crystals (melting point: 172–175° C.).

SYNTHESIS EXAMPLE III 2-(N-acetylaminomethyl)-7-cyclopentyl-4-ethyl-imidazo[4.5-e]-s-triazolo[1.5-a]pyrimidin-5-one 6-benzyl-2-(N-acetylaminomethyl )-7-cyclopentyl-4-ethyl-imidazo[4.5-e]-s-triazolo[1.5-a]pyrimidin-5-one 0.5 g of 2-aminomethyl-6-benzyl-7-cyclopentyl-4-ethyl-imidazo[4.5-e]-s-triazolo[1.5-a]pyrimidin-5-one (for preparation see synthesis example II) are dissolved in 10 ml of dichloromethane and 0.2 ml of pyridine, and 0.1 ml of acetyl chloride is added dropwise whilst cooling. After 2 hours' stirring at constant temperature the mixture is diluted with 10 ml of dichloromethane for working up and washed twice with dilute aqueous hydrochloric acid. The organic phase is separated off, dried over magnesium sulphate and the solvent is distilled off in vacuo. 0.7 g of the title compound are left in the form of an amorphous colourless solid.

2-(N-acetylaminomethyl)-7-cyclopentyl-4-ethyl-imidazo[4.5-e]s-triazolo[1.5a]pyrimidin-5-one 0.7 g of 6-benzyl-2-(N-acetylaminomethyl)-7-cyclopentyl-4-ethyl-imidazo[4.5-e]-s-triazolo[1.5-a]pyrimidin-5-one are hydrogenated in 30 ml of glacial acetic acid on 50 mg of Pearlman catalyst (5 bar, 60° C., 5.3 hours). For working up, the catalyst is filtered off and the solvent is distilled off in vacuo. The crude product is purified by chromatography on silica gel (dichloromethane:methanol 95:5) and yields 0.3 g of the title compound in the form of colourless crystals (melting point: 269–271° C.).

SYNTHESIS EXAMPLE IV 2-aminomethyl-7-cyclopentyl-4-ethyl-imidazo[4.5-e]-s-triazolo[1.5-a]pyrimidin-5-one 2-aminomethyl-6-benzyl-7-cyclopentyl-4-ethyl-imidazo[4.5-e]-s-triazolo[1.5-a]pyrimidin-5-one 2 g of 6-benzyl-7-cyclopentyl-4-ethyl-2-formyl-imidazo[4.5-e]-s-triazolo[1.5-a]pyrimidin-5-one (for preparation see synthesis example II) are hydrogenated together with 1 g of ammonia in 30 ml of methanol on 0.2 g of 10% palladium on charcoal (5 bar, 20° C., 2.3 hours). For working up, the catalyst is filtered off and the solvent is distilled off in vacuo. The crude product is purified by chromatography on silica gel (dichloromethane:methanol 95:5) and yields 0.65 g of the title compound in the form of a colourless amorphous solid.

2-aminomethyl-7-cyclopentyl-4-ethyl-imidazo[4.5-e]-s-triazolo[1.5-a]pyrimidin-5-one 0.56 g of 2-aminomethyl-6-benzyl-7-cyclopentyl-4-ethyl-imidazo[4.5-e]-s-triazolo[1.5-a]pyrimidin-5-one are hydrogenated in 30 ml of glacial acetic acid on 1 g of 10% palladium on charcoal (5 bar, 60° C., 6.4 hours). For working up, the catalyst is filtered off and the solvent is distilled off in vacuo. The crude product is purified by chromatography on silica gel (dichloromethane:methanol 90:10) and yields 0.18 g of the title compound in the form of colourless crystals (melting point: 240–245° C.).

Synthesis Example V 7-cyclopentyl-4-ethyl-2-(N-pyrrolylmethyl)-imidazo[4.5-e]-s-triazolo[1.5-a]pyrimidin-5-one 6-benzyl-7-cyclopentyl-4-ethyl-2-(N-pyrrolylmethyl)-imidazo[4.5-e]-s-triazolo[10.5-a]pyrimidin-5-one 48 mg of sodium hydride (60% in mineral oil) are added to a solution of 0.8 g of pyrrole in 10 ml of dimethylformamide. After 30 minutes' stirring at ambient temperature, 0.46 g of 6-benzyl-2-bromomethyl-7-cyclopentyl-4-ethyl-imidazo[4.5-e]-s-triazolo[1.5-a]pyrimidin-5-one is added (for preparation see Synthesis Example 1). The mixture is stirred at elevated temperature (about 60° C.) until the reaction is complete (about 6 hours). For working up, some water is added and then the solvent is distilled off in vacuo. The residue remaining is taken up in 15 ml of dichloromethane and 10 ml of water. After acidification with aqueous, 1N HCl solution the organic phase is separated off, washed with water and dried over magnesium sulphate. The solvent is distilled off and the residue remaining is purified by chromatography on silica gel (ethyl acetate:cyclohexane 1:1). 0.2 g of the title compound are obtained in the form of a colourless solid.

7-cyclopentyl-4-ethyl-2-(N-pyrrolylmethyl)-imidazo[4.5-e]-s-triazolo[1.5-a]pyrimidin-5-one 1 g of 6-benzyl-7-cyclopentyl-4-ethyl-2-(N-pyrrolylmethyl)-imidazo[4.5-e]-s-triazolo[1.5-a]pyrimidin-5-one is hydrogenated in 100 ml of methanol on 0.1 g of Pearlman catalyst (60° C., 5 bar, 4.5 hours). After the catalyst has been separated off the residue is evaporated to dryness. The title compound is purified by chromatography on silica gel (dichloromethane:methanol 97:3). Using the above method 0.67 g of the title compound (melting point:282–283° C.) was obtained.

Synthesis Example VI 2-(2-Aminoethyl)-7-cyclopentyl-4-ethyl-imidazo[4.5-e]-s-triazolo[1.5-a]pyrimidin-5-one 6-Benzyl-2-cyanomethyl-7-cyclopentyl-4-ethyl-imidazo[4.5-e]-s-triazolo[1.5-a]pyrimidin-5-one 0.46 g of 6-benzyl-2-bromomethyl-7-cyclopentyl-4-ethyl-imidazo[4.5-e]-s-triazolo[1.5-a]pyrimidin-5-one (for preparation see Synthesis example 1) are added to a solution of 0.72 g of KCN in 0.7 ml of water and 2.4 ml of ethanol heated to boiling. The mixture is boiled for a further 30 minutes until the reaction is complete. For working up the mixture is diluted with 10 ml of water and extracted with 15 ml of dichloromethane. The organic phase is separated off, washed with saturated sodium chloride solution and dried over magnesium sulphate. The solvent is distilled off and the residue remaining is purified by chromatography on silica gel (dichloromethane:methanol 99:1). 0.3 g of the title compound is obtained in the form of a colourless solid.

2-(2-Aminoethyl)-7-cyclopentyl-4-ethyl-imidazo[4.5-e]-s-triazolo[1.5-a]pyrimidin-5-one 0.26 g of 6-benzyl-2-cyanomethyl-7-cyclopentyl-4-ethyl-imidazo[4.5-e]-s-triazolo[1.5-a]pyrimidin-5-one is hydrogenated in 30 ml of methanol and 1 ml of concentrated hydrochloric acid (32%) on 50 mg of palladium catalyst (10%) (60° C., 5 bar, 3.3 hours). After the catalyst has been separated of the residue is evaporated to dryness. The title compound is purified by crystallisation from methanol. Using the above method, 0.23 g of the title compound were obtained (melting point: 272–275° C.).

The compounds of general formula (I) listed in Table 1 were prepared using the methods described above or by adopting analogous methods.

TABLE 1

(I)

| No. | R¹ | R² | R³ | R⁴ (or R⁶) | R⁵ | m.p. [° C.] | name |
|---|---|---|---|---|---|---|---|
| 1 | H | R² or R³ = H | | H | H | >300 | Imidazo[4.5-e]-s-triazolo[1.5-a]pyrimidin-5-one |
| 2 | H | R² or R³ = H | | H | Cyclopentyl | >360 | 7-Cyclopentyl-imidazo[4.5-e]-s-triazolo[1.5-a]pyrimidin-5-one |
| 3 | H | Ethyl | — | H | Cyclopentyl | 260 | 7-Cyclopentyl-3-ethyl-imidazo[4.5-e]-s-triazolo[1.5-a]pyrimidin-5-one |
| 4 | H | n-Propyl | — | H | Cyclopentyl | 217–220 | 7-Cyclopentyl-3-n-propyl-imidazo[4.5-e]-s-triazolo[1.5-a]pyrimidin-5-one |
| 5 | H | t-Butyl | — | H | Cyclopentyl | 149-150 | 3-t-Butyl-7-Cyclopentyl-imidazo[4.5-e]-s-triazolo[1.5-a]pyrimidin-5-one |
| 6 | H | — | Methyl | H | Cyclopentyl | 285 | 7-Cyclopentyl-4-methyl-imidazo[4.5-e]-s-triazolo[1.5-a]pyrimidin-5-one |
| 7 | H | — | Methyl | H | Benzyl | 306 | 7-Benzyl-4-methyl-imidazo[4.5-e]-s-triazolo[1.5-a]pyrimidin-5-one |
| 8 | H | — | Methyl | Methyl | Cyclopentyl | 206 | 7-Cyclopentyl-4,6-dimethyl-imidazo[4.5-e]-s-triazolo[1.5-a]pyrimidin-5-one |
| 9 | H | — | Ethyl | H | Cyclopentyl | 249–253 | 7-Cyclopentyl-4-ethyl-imidazo[4.5-e]-s-triazolo[1.5-a]pyrimidin-5-one |
| 10 | H | — | n-Propyl | H | Cyclopentyl | 250 | 7-Cyclopentyl-4-n-propyl-imidazo[4.5-e]-s-triazolo[1.5-a]pyrimidin-5-one |
| 11 | H | — | n-Propyl | H | Benzyl | 222–223 | 7-Benzyl-4-n-propyl-imidazo[4.5-e]-s-triazolo[1.5-a]pyrimidin-5-one |
| 12 | H | — | n-Butyl | H | Cyclopentyl | 243 | 4-n-Butyl-7-Cyclopentyl-imidazo[4.5-e]-s-triazolo[1.5-a]pyrimidin-5-one |
| 13 | H | — | t-Butyl | H | Cyclopentyl | 190–191 | 4-t-Butyl-7-Cyclopentyl-imidazo[4.5-e]-s-triazolo[1.5-a]pyrimidin-5-one |
| 14 | Methyl | — | n-Propyl | H | Cyclopentyl | 262–264 | 7-Cyclopentyl-2-methyl-4-n-propyl-imidazo[4.5-e]-s-triazolo[1.5-a]pyrimidin-5-one |
| 15 | Ethyl | — | n-Propyl | H | H | >300 | 2-Ethyl-4-n-propyl-imidazo[4.5-e]-s-triazolo[1.5-a]pyrimidin-5-one |
| 16 | Ethyl | — | n-Propyl | H | Ethyl | 229 | 2,7-Diethyl-4-n-propyl-imidazo[4.5-e]-s-triazolo[1.5-a]pyrimidin-5-one |
| 17 | Ethyl | — | n-Propyl | H | Cyclopentyl | 253 | 7-Cyclopentyl-2-ethyl-4-n-propyl-imidazo[4.5-e]-s-triazolo[1.5-a]pyrimidin-5-one |

TABLE 1-continued (I)

| No. | R¹ | R² | R³ | R⁴ (or R⁶) | R⁵ | m.p. [° C.] | name |
|---|---|---|---|---|---|---|---|
| 18 | n-Propyl | — | n-Propyl | H | Cyclopentyl | 256 | 7-Cyclopentyl-2,4-di-n-propyl-imidazo[4.5-e]-triazolo[1.5-a]pyrimidin-5-one |
| 19 | n-Propyl | — | n-Propyl | H | Phenyl | 300 Decomp. | 7-Phenyl-2,4-di-n-propyl-imidazo[4.5-e]-s-triazolo[1.5-a]pyrimidin-5-one |
| 20 | n-Propyl | — | n-Propyl | H | Benzyl | 221 | 7-Benzyl-2,4-di-n-propyl-imidazo[4.5-e]-s-triazolo[1.5-a]pyrimidin-5-one |
| 21 | i-Propyl | — | n-Propyl | H | Cyclopentyl | 260–261 | 7-Cyclopentyl-2-i-propyl-4-n-propyl-imidazo[4.5-e]-s-triazolo[1.5-a]pyrimidin-5-one |
| 22 | n-Butyl | — | n-Propyl | H | Cyclopentyl | 246 | 2-n-Butyl-7-cyclopentyl-4-n-propyl-imidazo[4.5-e]-s-triazolo[1.5-a]pyrimidin-5-one |
| 23 | t-Butyl | — | n-Propyl | H | Cyclopentyl | 310 | 2-t-Butyl-7-cyclopentyl-4-n-propyl-imidazo[4.5-e]-s-triazolo[1.5-a]pyrimidin-5-one |
| 24 | Cyclopentyl | R² or R³ = H | | H | H | 215 | 2-Cyclopentyl-imidazo[4.5-e]-s-triazolo[1.5-a]pyrimidin-5-one |
| 25 | Cyclopentyl | R² or R³ = H | | n-Propyl | H | 271–273 | 2-Cyclopentyl-6-n-propyl-imidazo[4.5-e]-s-triazolo[1.5-a]pyrimidin-5-one |
| 26 | Cyclopentyl | n-Propyl | — | H | H | 202–203 | 2-Cyclopentyl-3-n-propyl-imidazo[4.5-e]-s-triazolo[1.5-a]pyrimidin-5-one |
| 27 | Cyclopentyl | — | Methyl | H | H | >300 | 2-Cyclopentyl-4-methyl-imidazo[4.5-e]-s-triazolo[1.5-a]pyrimidin-5-one |
| 28 | Cyclopentyl | — | n-Propyl | H | H | 287 Decomp. | 2-Cyclopentyl-4-n-propyl-imidazo[4.5-e]-s-triazolo[1.5-a]pyrimidin-5-one |
| 29 | Cyclopentyl | — | n-Propyl | n-Propyl | H | 146 | 2-Cyclopentyl-4,6-di-n-propyl-imidazo[4.5-e]-s-triazolo[1.5-a]pyrimidin-5-one |
| 30 | Cyclopentyl | — | n-Propyl | n-Propyl | H | 151 | 2-Cyclopentyl-4,8-di-n-propyl-imidazo[4.5-e]-s-triazolo[1.5-a]pyrimidin-5-one |
| 31 | Cyclopentyl | — | n-Propyl | H | Methyl | 248–250 | 2-Cyclopentyl-7-methyl-4-n-propyl-imidazo[4.5-e]-s-triazolo[1.5-a]pyrimidin-5-one |

TABLE 1-continued

(I)

| No. | R¹ | R² | R³ | R⁴ (or R⁶) | R⁵ | m.p. [° C.] | name |
|---|---|---|---|---|---|---|---|
| 32 | Cyclopentyl | — | n-Propyl | H | Ethyl | 245–248 | 2-Cyclopentyl-7-ethyl-4-n-propyl-imidazo[4.5-e]-s-triazolo[1.5-a]pyrimidin-5-one |
| 33 | Cyclopentyl | — | n-Propyl | Methyl | Ethyl | 155–157 | 2-Cyclopentyl-7-ethyl-6-methyl-4-n-propyl-imidazo[4.5-e]-s-triazolo[1.5-a]pyrimidin-5-one |
| 34 | Cyclopentyl | — | n-Propyl | H | n-Propyl | 244–246 | 2-Cyclopentyl-4,7-di-n-propyl-imidazo[4.5-e]-s-triazolo[1.5-a]pyrimidin-5-one |
| 35 | Cyclopentyl | — | n-Propyl | H | Cyclopentyl | 306–308 | 2,7-Dicyclopentyl-4-n-propyl-imidazo[4.5-e]-s-triazolo[1.5-a]pyrimidin-5-one |
| 36 | Cyclopentyl | — | n-Propyl | H | tetrahydrofuranyl | 289–290 | 2-Cyclopentyl-4-n-propyl-7-(3-tetrahydrofuranyl)-imidazo[4.5-e]-s-triazolo[1.5-a]pyrimidin-5-one |
| 37 | Cyclopentyl | — | n-Propyl | H | Benzyl | 233 | 7-Benzyl-2-cyclopentyl-4-n-propyl-imidazo[4.5-e]-s-triazolo[1.5-a]pyrimidin-5-one |
| 38 | Cyclopentyl | — | i-Propyl | H | Ethyl | 260–262 | 2-Cyclopentyl-7-ethyl-4-i-propyl-imidazo[4.5-e]-s-triazolo[1.5-a]pyrimidin-5-one |
| 39 | Cyclopentyl | — | n-Butyl | H | Ethyl | 265 | 4-n-Butyl-2-cyclopentyl-7-ethyl-imidazo[4.5-e]-s-triazolo[1.5-a]pyrimidin-5-one |
| 40 | Cyclopentyl | — | i-Butyl | H | Ethyl | 297 | 4-i-Butyl-2-cyclopentyl-7-ethyl-imidazo[4.5-e]-s-triazolo[1.5-a]pyrimidin-5-one |
| 41 | Cyclopentyl | — | n-Pentyl | H | Ethyl | 255 | 2-Cyclopentyl-7-ethyl-4-n-pentyl-imidazo[4.5-e]-s-triazolo[1.5-a]pyrimidin-5-one |
| 42 | Cyclopentyl | — | 1-Buten-4-yl | H | Ethyl | 243 | 4-(1-Buten-4-yl)-2-cyclopentyl-7-ethyl-imidazo[4.5-e]-s-triazolo[1.5-a]pyrimidin-5-one |

TABLE 1-continued (I)

| No. | $R^1$ | $R^2$ | $R^3$ | $R^4$ (or $R^6$) | $R^5$ | m.p. [° C.] | name |
|---|---|---|---|---|---|---|---|
| 43 | Cyclohexylmethyl | — | Ethyl | H | H | 328–330 | 2-Cyclohexylmethyl-4-ethyl-imidazo[4.5-e]-s-triazolo[1.5-a]pyrimidin-5-one |
| 44 | Cyclohexylmethyl | — | Ethyl | H | Ethyl | 230–232 | 2-Cyclohexylmethyl-4,7-diethyl-imidazo[4.5-e]-s-triazolo[1.5-a]pyrimidin-5-one |
| 45 | Cyclohexylmethyl | — | Ethyl | H | Cyclopentyl | 273–274 | 2-Cyclohexylmethyl-7-cyclopentyl-4-ethyl-imidazo[4.5-e]-s-triazolo[1.5-a]pyrimidin-5-one |
| 46 | Cyclohexylmethyl | — | Ethyl | H | norbornenyl | 246–248 | 2-Cyclohexylmethyl-4-ethyl-7-(5-norbornen-2(S)-yl)-imidazo[4.5-e]-s-triazolo[1.5-a]pyrimidin-5-one |
| 47 | Cyclohexylmethyl | — | Ethyl | H | norbornenyl | 258–260 Decomp. | 2-Cyclohexylmethyl-4-ethyl-7-(5-norbornen-2(R)-yl)-imidazo[4.5-e]-s-triazolo[1.5-a]pyrimidin-5-one |
| 48 | Benzyl | $R^2$ or $R^3$ = H | | H | H | >300 | 2-Benzyl-imidazo[4,5-e]-s-triazolo[1.5-a]pyrimidin-5-one |
| 49 | Benzyl | $R^2$ or $R^3$ = H | | H | Cyclopentyl | 270 Decomp. | 2-Benzyl-7-cyclopentyl-imidazo[4.5-e]-s-triazolo[1.5-a]pyrimidin-5-one |
| 50 | Benzyl | — | Methyl | H | H | >300 | 2-Benzyl-4-methyl-imidazo[4.5-e]-s-triazolo[1.5-a]pyrimidin-5-one |
| 51 | Benzyl | — | Methyl | H | Cyclopentyl | 265–267 | 2-Benzyl-7-cyclopentyl-4-methyl-imidazo [4.5-e]-s-triazolo[1.5-a]pyrimidin-5-one |
| 52 | Benzyl | — | Ethyl | H | t-Butyl | 243–244 | 2-Benzyl-7-t-butyl-4-ethyl-imidazo[4.5-e]-s-triazolo[1.5-a]pyrimidin-5-one |

TABLE 1-continued

(I)

| No. | R¹ | R² | R³ | R⁴ (or R⁶) | R⁵ | m.p. [° C.] | name |
|---|---|---|---|---|---|---|---|
| 53 | Benzyl | — | Ethyl | H | Cyclopentyl | 242 | 2-Benzyl-7-cyclopentyl-4-ethyl-imidazo[4.5-e]-s-triazolo[1.5-a]pyrimidin-5-one |
| 54 | Benzyl | — | Ethyl | H | Cyclohexyl | 260–262 | 2-Benzyl-7-cyclohexyl-4-ethyl-imidazo[4.5-e]-s-triazolo[1.5-a]pyrimidin-5-one |
| 55 | Benzyl | — | Ethyl | H |  | 320–322 | 2-Benzyl-4-ethyl-7-(noradamantan-3-yl)-imidazo[4.5-e]-s-triazolo[1.5-a]pyrimidin-5-one |
| 56 | Benzyl | — | Ethyl | H | Phenyl | 343–345 | 2-Benzyl-4-ethyl-7-phenyl-imidazo[4.5-e]-s-triazolo[1.5-a]pyrimidin-5-one |
| 57 | Benzyl | — | Ethyl | H |  | 237 | 2-Benzyl-4-ethyl-7-(3-tetrahydrofuranyl)-imidazo[4.5-e]-s-triazolo[1.5-a]pyrimidin-5-one |
| 58 | Benzyl | — | Ethyl | H |  | 227 | 2-Benzyl-4-ethyl-7-(4-tetrahydropyranyl)-imidazo[4.5-e]-s-triazolo[1.5-a]pyrimidin-5-one |
| 59 | Benzyl | — | Ethyl | H |  | 287 | 2-Benzyl-4-ethyl-7-(2-pyridyl)-imidazo[4.5-e]-s-triazolo[1.5-a]pyrimidin-5-one |
| 60 | Benzyl | — | Ethyl | H |  | 331–332 | 2-Benzyl-4-ethyl-7-(3-pyridyl)-imidazo[4.5-e]-s-triazolo[1.5-a]pyrimidin-5-one |

TABLE 1-continued (I)

[Structure shown: imidazo-triazolo-pyrimidinone core with substituents R¹ at position 2, R² at position 3, R³ at position 4, R⁴ (or R⁶) at position 6 (N⁶), R⁵ at position 7, and ring atoms N₁, N₂, C₃, N₄, C₅(=O), N₆, C₇, N₈]

| No. | R¹ | R² | R³ | R⁴ (or R⁶) | R⁵ | m.p. [° C.] | name |
|---|---|---|---|---|---|---|---|
| 61 | Benzyl | — | Ethyl | H | 4-pyridyl | 346 | 2-Benzyl-4-ethyl-7-(4-pyridyl)-imidazo[4.5-e]-s-triazolo[1.5-a]pyrimidin-5-one |
| 62 | Benzyl | — | Ethyl | Ethyl | H | >300 | 2-Benzyl-4,6-diethyl-imidazo[4.5-e]-s-triazolo[1.5-a]pyrimidin-5-one |
| 63 | Benzyl | — | Ethyl | Ethyl | 2-furanyl | 187–189 | 2-Benzyl-4,6-diethyl-7-(2-furanyl)-imidazo[4.5-e]-s-triazolo[1.5-a]pyrimidin-5-one |
| 64 | Benzyl | — | n-Propyl | H | Methyl | 231–233 | 2-Benzyl-7-methyl-4-n-propyl-imidazo[4.5-e]-s-triazolo[1.5-a]pyrimidin-5-one |
| 65 | Benzyl | — | -n-Propyl | H | H | >300 | 2-Benzyl-4-n-propyl-imidazo[4.5-e]-s-triazolo[1.5-a]pyrimidin-5-one |
| 66 | Benzyl | — | -n-Propyl | H | -Ethyl | 223 | 2-Benzyl-7-ethyl-4-n-propyl-imidazo[4.5-e]-s-triazolo[1.5-a]pyrimidin-5-one |
| 67 | Benzyl | — | n-Propyl | Methyl | Ethyl | 167–169 | 2-Benzyl-7-ethyl-6-methyl-4-n-propyl-imidazo[4.5-e]-s-triazolo[1.5-a]pyrimidin-5-one |
| 68 | Benzyl | — | -n-Propyl | H | -n-Propyl | 202 | 2-Benzyl-4,7-di-n-propyl-imidazo[4.5-e]-s-triazolo[1.5-a]pyrimidin-5-one |
| 69 | Benzyl | — | -n-Propyl | H | Cyclopentyl | 234–235 | 2-Benzyl-7-cyclopentyl-4-n-propyl-imidazo[4.5-e]-s-triazolo[1.5-a]pyrimidin-5-one |
| 70 | Benzyl | — | n-Propyl | H | —N(CH₃)₂ | 272–274 | 2-Benzyl-7-dimethylamino-4-n-propyl-imidazo[4.5-e]-s-triazolo[1.5-a]pyrimidin-5-one |

TABLE 1-continued (I)

[Structure: imidazo-triazolo-pyrimidinone core with substituents R¹, R², R³, R⁴ (or R⁶), R⁵]

| No. | R¹ | R² | R³ | R⁴ (or R⁶) | R⁵ | m.p. [° C.] | name |
|---|---|---|---|---|---|---|---|
| 71 | Benzyl | — | -n-Propyl | H | N-methylpiperidinyl | 294–297 | 2-Benzyl-7-(N-piperidinyl)-4-n-propyl-imidazo[4.5-e]-s-triazolo[1.5-a]pyrimidin-5-one |
| 72 | Benzyl | — | -n-Propyl | H | N-methylmorpholino | 298 | 2-Benzyl-7-(N-morpholino)-4-n-propyl-imidazo[4.5-e]-s-triazolo[1.5-a]pyrimidin-5-one |
| 73 | Benzyl | — | n-Propyl | H | N-methylpiperazinyl | 260 | 2-Benzyl-7-(piperazin-1-yl)-4-n-propyl-imidazo[4.5-e]-s-triazolo[1.5-a]pyrimidin-5-one |
| 74 | Benzyl | — | n-Propyl | H | 4-benzyl-N-methylpiperazinyl | 266–268 | 2-Benzyl-7-(4-benzylpiperazin-1-yl)-4-n-propyl-imidazo[4.5-e]-s-triazolo[1.5-a]pyrimidin-5-one |
| 75 | Benzyl | — | -i-Propyl | H | H | >300 | 2-Benzyl-4-i-propyl-imidazo[4.5-e]-s-triazolo[1.5-a]pyrimidin-5-one |
| 76 | Benzyl | — | -n-Butyl | H | H | >300 | 2-Benzyl-4-n-butyl-imidazo[4.5-e]-s-triazolo[1.5-a]pyrimidin-5-one |
| 77 | Benzyl | — | -n-Butyl | H | Cyclopentyl | 238–240 | 2-Benzyl-4-n-butyl-7-cyclopentyl-imidazo[4.5-e]-s-triazolo[1.5-a]pyrimidin-5-one |
| 78 | Benzyl | — | -n-Pentyl | H | Cyclopentyl | 231–236 | 2-Benzyl-7-cyclopentyl-4-n-pentyl-imidazo[4.5-e]-s-triazolo[1.5-a]pyrimidin-5-one |
| 79 | Benzyl | — | Benzyl | H | Cyclopentyl | 270 | 2,4-Dibenzyl-7-cyclopentyl-imidazo[4.5-e]-s-triazolo[1.5-a]pyrimidin-5-one |

TABLE 1-continued (I)

[Structure: imidazo-triazolo-pyrimidine core with substituents R¹ through R⁶]

| No. | R¹ | R² | R³ | R⁴ (or R⁶) | R⁵ | m.p. [° C.] | name |
|---|---|---|---|---|---|---|---|
| 80 | phenylethyl | — | -Ethyl | H | —H | 273 | 4-Ethyl-2-(2-phenylethyl)-imidazo[4,5-e]-s-triazolo[1,5-a]pyrimidin-5-one |
| 81 | phenylethyl | — | Ethyl | H | Methyl | 283–284 | 4-Ethyl-7-methyl-2-(2-phenylethyl)-imidazo[4,5-e]-s-triazolo[1,5-a]pyrimidin-5-one |
| 82 | phenylethyl | — | -Ethyl | H | -Ethyl | 282–283 | 4,7-Diethyl-2-(2-phenylethyl)-imidazo[4,5-e]-s-triazolo[1,5-a]pyrimidin-5-one |
| 83 | phenylethyl | — | Ethyl | H | n-Propyl | 250–253 | 4-Ethyl-2-(2-phenylethyl)-7-n-propyl-imidazo[4,5-e]-s-triazolo[1,5-a]pyrimidin-5-one |
| 84 | phenylethyl | — | Ethyl | H | Cyclopentyl | 292–294 | 7-Cyclopentyl-4-ethyl-2-(2-phenylethyl)-imidazo[4,5-e]-s-triazolo[1,5-a]pyrimidin-5-one |
| 85 | 4-hydroxybenzyl-ethyl | — | Ethyl | H | t-Butyl | 297–298 | 7-t-Butyl-4-ethyl-2-(4-hydroxybenzyl)-imidazo[4,5-e]-s-triazolo[1,5-a]pyrimidin-5-one |
| 86 | 4-hydroxybenzyl-ethyl | — | Ethyl | Methyl | t-Butyl | 202–204 | 7-t-Butyl-4-ethyl-2-(4-hydroxybenzyl)-6-methyl-imidazo[4,5-e]-s-triazolo[1,5-a]pyrimidin-5-one |

TABLE 1-continued (I)

Structure: fused ring system with R¹–R⁶ substituents (imidazo-triazolo-pyrimidinone core)

| No. | R¹ | R² | R³ | R⁴ (or R⁶) | R⁵ | m.p. [° C.] | name |
|---|---|---|---|---|---|---|---|
| 87 | 4-ethylphenyl-OH | — | Ethyl | 2-(N-propyl-morpholino)ethyl | t-Butyl | — | 7-t-Butyl-4-ethyl-2-(4-hydroxybenzyl)-6-[2-(N-morpholino)-ethyl]imidazo[4.5-e]-s-triazolo[1.5-a]pyrimidin-5-one |
| 88 | 4-ethylphenyl-OMe | — | Ethyl | H | t-Butyl | 204 Decomp. | 7-t-Butyl-4-ethyl-2-(4-methoxybenzyl)-imidazo[4.5-e]-s-triazolo[1.5-a]pyrimidin-5-one |
| 89 | 4-ethylphenyl-OMe | — | Ethyl | Methyl | t-Butyl | 127–128 | 7-t-Butyl-4-ethyl-2-(4-methoxybenzyl)-6-methyl-imidazo[4.5-e]-s-triazolo[1.5-a]pyrimidin-5-one |
| 90 | 4-ethylphenyl-OBn | — | Ethyl | H | t-Butyl | 245–246 | 2-(4-Benzyloxy-benzyl)-7-t-butyl-4-ethyl-imidazo[4.5-e]-s-triazolo[1.5-a]pyrimidin-5-one |
| 91 | 4-ethylphenyl-OBn | — | Ethyl | H | Cyclopentyl | 251 | 2-(4-Benzyloxy-benzyl)-7-cyclopentyl-4-ethyl-imidazo[4.5-e]-s-triazolo[1.5-a]pyrimidin-5-one |
| 92 | 4-ethylphenyl-OBn | — | Ethyl | Benzyl | Cyclopentyl | 138–140 | 8-Benzyl-2-(4-benzyloxy-benzyl)-7-cyclopentyl-4-ethyl-imidazo[4.5-e]-s-triazolo[1.5-a]pyrimidin-5-one |

TABLE 1-continued (I)

[Structure shown with R¹, R², R³, R⁴, R⁵, R⁶ substituents on imidazo/triazolo pyrimidine scaffold]

| No. | R¹ | R² | R³ | R⁴ (or R⁶) | R⁵ | m.p. [°C] | name |
|---|---|---|---|---|---|---|---|
| 93 | 4-(2-(dimethylamino)ethyloxy)benzyl (with NMe₂) | — | Ethyl | H | t-Butyl | 204 Decomp. | 7-t-Butyl-2-{4-[2-(dimethylamino)ethyloxy]-benzyl}-4-ethyl-imidazo[4.5-e]-s-triazolo[1.5-a]pyrimidin-5-one |
| 94 | 4-(2-(N-morpholino)ethyloxy)benzyl | — | Ethyl | H | t-Butyl | 228–230 | 7-t-Butyl-4-ethyl-2-{4-[2-(N-morpholino)-ethyloxy]-benzyl}-imidazo[4.5-e]-s-triazolo[1.5-a]pyrimidin-5-one |
| 95 | 4-fluorobenzyl | — | Ethyl | H | t-Butyl | 262–264 | 7-t-Butyl-4-ethyl-2-(4-fluorobenzyl)-imidazo[4.5-e]-s-triazolo[1.5-a]pyrimidin-5-one |
| 96 | 4-fluorobenzyl | — | Ethyl | H | Cyclopentyl | 252–254 | 7-Cyclopentyl-4-ethyl-2-(4-fluorobenzyl)-imidazo[4.5-e]-s-triazolo[1.5-a]pyrimidin-5-one |
| 97 | 4-fluorobenzyl | — | Ethyl | H | noradamantan-3-yl | 325–327 | 4-Ethyl-2-(4-fluorobenzyl)-7-(noradamantan-3-yl)-imidazo[4.5-e]-s-triazolo[1.5-a]pyrimidin-5-one |
| 98 | 4-fluorobenzyl | — | Ethyl | H | adamantan-1-yl | 337–339 | 7-(Adamantan-1-yl)-4-ethyl-2-(4-fluorobenzyl)-imidazo[4.5-e]-s-triazolo[1.5-a]pyrimidin-5-one |

TABLE 1-continued (I)

| No. | R¹ | R² | R³ | R⁴ (or R⁶) | R⁵ | m.p. [° C.] | name |
|---|---|---|---|---|---|---|---|
| 99 | 3,4-difluoro-phenyl (with ethyl) | — | Ethyl | H | Cyclopentyl | 264–266 | 7-Cyclopentyl-4-ethyl-2-(3,4-difluorobenzyl)-imidazo[4,5-e]-s-triazolo[1,5-a]pyrimidin-5-one |
| 100 | 3,4-difluoro-phenyl (with ethyl) | — | Ethyl | H | adamantyl | 315–317 | 4-Ethyl-2-(3,4-difluorobenzyl)-7-(nor-adamantan-3-yl)-imidazo[4 5-e]-s-triazolo[1,5-a]pyrimidin-5-one |
| 101 | 4-fluoro-phenyl (with ethyl) | — | Ethyl | H | norbornenyl | 255–257 | 4-Ethyl-2-(4-fluorobenzyl)-7-(5-nornornen-2(S)-yl)-imidazo[4,5-e]-s-triazolo[1,5-a]pyrimidin-5-one |
| 102 | Phenyl | — | n-Propyl | H | H | 295–296 Decomp. | 2-Phenyl-4-n-propyl-imidazo[4,5-e]-s-triazolo[1,5-a]pyrimidin-5-one |
| 103 | Phenyl | — | n-Propyl | H | Ethyl | >300 Decomp. | 7-Ethyl-2-phenyl-4-n-propyl-imidazo[4,5-e]-s-triazolo[1,5-a]pyrimidin-5-one |
| 104 | Phenyl | — | n-Propyl | H | Cyclopentyl | >300 Decomp. | 7-Cyclopentyl-2-phenyl-4-n-propyl-imidazo[4,5-e]-s-triazolo[1,5-a]pyrimidin-5-one |
| 105 | —CH₂—NH₂ | — | Ethyl | H | Cyclopentyl | 240–245 | 2-Aminomethyl-7-cyclopentyl-4-ethyl-imidazo[4,5-e]-s-triazolo[1,5-a]pyrimidin-5-one |
| 106 | —CH₂—NHMe | — | Ethyl | H | Cyclopentyl | 172–175 | 7-Cyclopentyl-4-ethyl-2-(methylaminomethyl)-imidazo[4,5-e]-s-triazolo[1,5-a]pyrimidin-5-one |
| 107 | —CH₂—NMe₂ | — | Ethyl | H | Cyclopentyl | 224–225 | 7-Cyclopentyl-4-ethyl-2-(dimethylaminomethyl)-imidazo[4,5-e]-s-triazolo[1,5-a]pyrimidin-5-one |

TABLE 1-continued

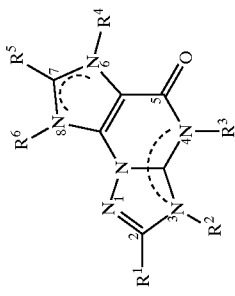

(I)

| No. | R¹ | R² | R³ | R⁴ (or R⁶) | R⁵ | m.p. [° C.] | name |
|---|---|---|---|---|---|---|---|
| 108 | —CH₂—NMe₂ | — | Ethyl | Benzyl | Cyclopentyl | — | 8-Benzyl-7-cyclopentyl-4-ethyl-2-(dimethylaminomethyl)-imidazo[4,5-e]-s-triazolo[1,5-a]pyrimidin-5-one |
| 109 | —CH₂—N(i-Pr)₂ | — | Ethyl | H | t-Butyl | 262–264 | 7-t-Butyl-4-ethyl-2-(diisopropylaminomethyl)-imidazo[4,5-e]-s-triazolo[1,5-a]pyrimidin-5-one |
| 110 | [4-methylpiperazin-1-yl, N-ethyl] | — | Ethyl | H | t-Butyl | 283 Decomp. | 7-t-Butyl-4-ethyl-2-[(4-methylpiperazin-1-yl)methyl]-imidazo[4,5-e]-s-triazolo[1,5-a]pyrimidin-5-one |
| 111 | [morpholino, N-ethyl] | — | Ethyl | H | Cyclopentyl | 184 | 7-Cyclopentyl-4-ethyl-2-(N-morpholino-methyl)-imidazo[4,5-e]-s-triazolo[1,5-a]pyrimidin-5-one |
| 112 | [morpholino, N-ethyl] | — | Ethyl | Benzyl | Cyclopentyl | — | 8-Benzyl-7-cyclopentyl-4-ethyl-2-(N-morpholino-methyl)-imidazo[4,5-e]-s-triazolo[1,5-a]pyrimidin-5-one |
| 113 | —CH₂—NHAc | — | Ethyl | H | Cyclopentyl | 269–271 | 2-(N-Acetylaminomethyl)-7-cyclopentyl-4-ethyl-imidazo[4,5-e]-s-triazolo[1,5-a]pyrimidin-5-one |
| 114 | —CH₂CH₂—NH₂ | — | Ethyl | H | Cyclopentyl | 272–275 | 2-(2-Aminoethyl)-7-cyclopentyl-4-ethyl-imidazo[4,5-e]-s-triazolo[1,5-a]pyrimidin-5-one |
| 115 | —CH₂—OH | — | Ethyl | H | t-Butyl | 236 | 7-t-Butyl-4-ethyl-2-hydroxymethyl-imidazo[4,5-e]-s-triazolo[1,5-a]pyrimidin-5-one |
| 116 | —CH₂—OH | — | Ethyl | H | Cyclopentyl | 305–307 | 7-Cyclopentyl-4-ethyl-2-hydroxymethyl-imidazo[4,5-e]-s-triazolo[1,5-a]pyrimidin-5-one |

TABLE 1-continued (I)

[Structure: imidazo-triazolo-pyrimidinone core with positions N1, N2(R2), N3, N4(R3), C5=O, N6(R4 or R6), C7(R5), N8, and R1 at position 2]

| No. | R¹ | R² | R³ | R⁴ (or R⁶) | R⁵ | m.p. [° C.] | name |
|---|---|---|---|---|---|---|---|
| 117 | —CH₂—OH | — | Ethyl | Benzyl | Cyclopentyl | 204–207 | 8-Benzyl-7-cyclopentyl-4-ethyl-2-hydroxymethyl-imidazo[4.5-e]-s-triazolo[1.5-a]pyrimidin-5-one |
| 118 | —CH₂—OMe | — | Ethyl | H | Cyclopentyl | 246–248 | 7-Cyclopentyl-4-ethyl-2-methoxymethyl-imidazo[4.5-e]-s-triazolo[1.5-a]pyrimidin-5-one |
| 119 | —CH₂—OMe | — | Ethyl | Benzyl | Cyclopentyl | 116–118 | 8-Benzyl-7-cyclopentyl-4-ethyl-2-methoxymethyl-imidazo[4.5-e]-s-triazolo[1.5-a]pyrimidin-5-one |
| 120 | —CH₂—OEt | — | Ethyl | H | Cyclopentyl | 224–225 | 7-Cyclopentyl-2-ethoxymethyl-4-ethyl-imidazo[4.5-e]-s-triazolo[1.5-a]pyrimidin-5-one |
| 121 | —CH₂—OEt | — | Ethyl | Benzyl | Cyclopentyl | 120–123 | 8-Benzyl-7-cyclopentyl-2-ethoxymethyl-4-ethyl-imidazo[4.5-e]-s-triazolo[1.5-a]pyrimidin-5-one |
| 122 | —CH(OH)Me | — | Ethyl | H | Cyclopentyl | 264–266 | 7-Cyclopentyl-4-ethyl-2-(1-hydroxyethyl)-imidazo[4.5-e]-s-triazolo[1.5-a]pyrimidin-5-one |
| 123 | —CH₂—OPhenyl | — | Ethyl | H | Cyclopentyl | 229 | 7-Cyclopentyl-4-ethyl-2-phenyloxymethyl-imidazo[4.5-e]-s-triazolo[1.5-a]pyrimidin-5-one |
| 124 | 4-OCH₃-phenyl-O-ethyl | — | Ethyl | H | Ethyl | 225 | 4,7-Diethyl-2-(4-methoxyphenyloxymethyl)-imidazo[4.5-e]-s-triazolo[1.5-a]pyrimidin-5-one |
| 125 | 4-OCH₃-phenyl-O-ethyl | — | Ethyl | H | Cyclopentyl | 234–236 | 7-Cyclopentyl-4-ethyl-2-(4-methoxyphenyloxymethyl)-imidazo[4.5-e]-s-triazolo[1.5-a]pyrimidin-5-one |
| 126 | 4-OCH₃-phenyl-O-ethyl | — | Ethyl | H | Cyclopentyl | 182 | 7-Cyclopentyl-4-ethyl-2-(4-methoxybenzyloxymethyl)-imidazo[4.5-e]-s-triazolo[1.5-a]pyrimidin-5-one |

TABLE 1-continued (I)

| No. | $R^1$ | $R^2$ | $R^3$ | $R^4$ (or $R^6$) | $R^5$ | m.p. [° C.] | name |
|---|---|---|---|---|---|---|---|
| 127 | 4-OCH₃, 4-OEt phenyl | — | Ethyl | Benzyl | Cyclopentyl | 127–128 | 8-Benzyl-7-cyclopentyl-4-ethyl-2-(4-methoxy-benzyloxymethyl)-imidazo[4.5-e]-s-triazolo[1.5-a]pyrimidin-5-one |
| 128 | —CH₂Br | — | Ethyl | Benzyl | Cyclopentyl | 188–189 | 8-Benzyl-2-bromomethyl-7-cyclopentyl-4-ethyl-imidazo[4.5-e]-s-triazolo[1.5-a]pyrimidin-5-one |
| 129 | —CHO | — | Ethyl | Benzyl | Cyclopentyl | 153–154 | 8-Benzyl-7-cyclopentyl-4-ethyl-2-formyl-imidazo[4.5-e]-s-triazolo[1.5-a]pyrimidin-5-one |
| 130 | —COOH | — | Ethyl | H | Cyclopentyl | >300 | 2-Carboxy-7-cyclopentyl-4-ethyl-imidazo[4.5-e]-s-triazolo[1.5-a]pyrimidin-5-one |
| 131 | —COOH | — | Ethyl | Benzyl | Cyclopentyl | 157–158 | 8-Benzyl-2-carboxy-7-cyclopentyl-4-ethyl-imidazo[4.5-e]-s-triazolo[1.5-a]pyrimidin-5-one |
| 132 | —COOMe | — | Ethyl | H | Cyclopentyl | 270–271 | 2-Carboxymethyl-7-cyclopentyl-4-ethyl-imidazo[4.5-e]-s-triazolo[1.5-a]pyrimidin-5-one |
| 133 | —COOMe | — | Ethyl | Benzyl | Cyclopentyl | 155–157 | 8-Benzyl-2-carboxymethyl-7-cyclopentyl-4-ethyl-imidazo[4.5-e]-s-triazolo[1.5-a]pyrimidin-5-one |
| 134 | COO-iPropyl | — | Ethyl | H | t-Butyl | 298–302 | 7-t-butyl-2-carboxyisopropyl-4-ethyl-imidazo[4.5-e]-s-triazolo[1.5-a]pyrimidin-5-one |
| 135 | COO-iPropyl | — | Ethyl | H | Cyclopentyl | 304–305 | 2-Carboxyisopropyl-7-cyclopentyl-4-ethyl-imidazo[4.5-e]-s-triazolo[1.5-a]pyrimidin-5-one |
| 136 | COO-t-Butyl | — | Ethyl | H | t-Butyl | >300 | 7-t.-Butyl-2-(carboxy-tert.butyl)-4-ethyl-imidazo[4.5-e]-s-triazolo[1.5-a]pyrimidin-5-one |
| 137 | COO-t-Butyl | — | Ethyl | H | Cyclopentyl | >300 | 2-(Carboxy-tert.butyl)-7-cyclopentyl-4-ethyl-imidazo[4.5-e]-s-triazolo[1.5-a]pyrimidin-5-one |

TABLE 1-continued (I)

[structure: fused ring system with R¹ at position 2, R² at 3, R³ at 4 (or R⁶ N), carbonyl at 5, R⁴ (or R⁶) on N6, R⁵ at 7, R⁶ on N8]

| No. | R¹ | R² | R³ | R⁴ (or R⁶) | R⁵ | m.p. [° C.] | name |
|---|---|---|---|---|---|---|---|
| 138 | benzoyloxymethyl (PhC(O)OCH₂–) | — | Ethyl | H | Cyclopentyl | 238–239 | 2-(Benzoyloxymethyl)-7-cyclopentyl-4-ethyl-imidazo[4,5-e]-s-triazolo[1,5-a]pyrimidin-5-one |
| 139 | benzoyloxymethyl | — | Ethyl | Benzyl | Cyclopentyl | — | 2-(Benzoyloxymethyl)-8-benzyl-7-cyclopentyl-4-ethyl-imidazo[4,5-e]-s-triazolo[1,5-a]pyrimidin-5-one |
| 140 | 3-pyridylcarbonyloxymethyl | — | Ethyl | Benzyl | Cyclopentyl | — | 8-Benzyl-7-cyclopentyl-4-ethyl-2-(3-pyridylcarbonyloxy-methyl)-imidazo[4,5-e]-s-triazolo[1,5-a]pyrimidin-5-one |
| 141 | 3-pyridylmethyl | — | Ethyl | H | H | 328–330 | 4-Ethyl-2-(3-pyridylmethyl)-imidazo[4,5-e]-s-triazolo[1,5-a]pyrimidin-5-one |
| 142 | 3-pyridylmethyl | — | Ethyl | H | Ethyl | 225–227 | 4,7-Diethyl-2-(3-pyridylmethyl)-imidazo[4,5-e]-s-triazolo[1,5-a]pyrimidin-5-one |

TABLE 1-continued (I)

| No. | R¹ | R² | R³ | R⁴ (or R⁶) | R⁵ | m.p. [° C.] | name |
|---|---|---|---|---|---|---|---|
| 143 | 3-pyridyl-ethyl | — | Ethyl | H | Cyclopentyl | 261–263 | 7-Cyclopentyl-4-ethyl-2-(3-pyridyl-methyl)-imidazo[4.5-e]-s-triazolo[1.5-a]pyrimidin-5-one |
| 144 | 3-pyridyl-ethyl | — | Ethyl | H | 3-noradamantyl | 330–332 | 4-Ethyl-7-(noradamantan-3-yl)-(3-pyridylmethyl)-imidazo[4.5-e]-s-triazolo[1.5-a]pyrimidin-5-one |
| 145 | 3-pyridyl-N-ethyl | — | Ethyl | Benzyl | Cyclopentyl | — | 8-Benzyl-7-cyclopentyl-4-ethyl-2-[N-(3-pyridyl)amino-methyl]-imidazo[4.5-e]-s-triazolo[1.5-a]pyrimidin-5-one |
| 146 | 1-pyrrolyl-ethyl | — | Ethyl | H | Cyclopentyl | 282–283 | 7-Cyclopentyl-4-ethyl-2-(N-pyrrolylmethyl)-imidazo[4.5-e]-s-triazolo[1.5-a]pyrimidin-5-one |
| 147 | 1-pyrrolyl-ethyl | — | Ethyl | Benzyl | Cyclopentyl | 137–138 | 8-Benzyl-7-cyclopentyl-4-ethyl-2-(N-pyrrolylmethyl)-imidazo[4.5-e]-s-triazolo[1.5-a]pyrimidin-5-one |
| 148 | 2-Furanyl | — | n-Propyl | H | H | >300 Decomp. | 2-(2-Furanyl)-4-n-propyl-imidazo[4.5-e]-s-triazolo[1.5-a]pyrimidin-5-one |
| 149 | 2-Furanyl | — | n-Propyl | H | Methyl | >300 | 2(2-Furanyl)-7-methyl-4-propyl-imidazo[4.5-e]-triazolo[1.5-a]pyrimidin-5-one |
| 150 | 2-Furanyl | — | n-Propyl | H | Ethyl | >300 Decomp. | 7-Ethyl-2-(2-furanyl)-4-n-propyl-imidazo[4.5-e]-s-triazolo[1.5-a]pyrimidin-5-one |
| 151 | 2-Furanyl | — | n-Propyl | H | n-Propyl | >300 | 2-(2-Furanyl)-4,7-di-n-propyl-imidazo[4.5-e]-s-triazolo[1.5-a]pyrimidin-5-one |

TABLE 1-continued (I)

| No. | R¹ | R² | R³ | R⁴ (or R⁶) | R⁵ | m.p. [° C.] | name |
|---|---|---|---|---|---|---|---|
| 152 | 2-Furanyl | — | n-Propyl | H | Cyclopentyl | >300 Decomp. | 7-Cyclopentyl-2-(2-furanyl)-4-n-propyl-imidazo[4,5-e]-s-triazolo[1,5-a]pyrimidin-5-one |
| 153 | 2-Furanyl | — | n-Propyl | H | 2-Furanyl | 385–387 | 2,7-Di-(2-furanyl)-4-n-propyl-imidazo[4,5-e]-triazolo[1,5-a]pyrimidin-5-one |
| 154 | Cyclopentyl | — | Allyl | H | Ethyl | 231–232 | 2-Cyclopentyl-7-ethyl-4-(1-propen-3-yl)-imidazo[4,5-e]-triazolo[1,5-a]pyrimidin-5-one |
| 155 | Cyclopentyl | — | Propargyl | H | Ethyl | 274 | 2-Cyclopentyl-7-ethyl-4-(1-propin-3-yl)-imidazo[4,5-e]-s-triazolo[1,5-a]pyrimidin-5-one |
| 156 | Cyclopentyl | — | 2-Methoxy-ethyl | H | Ethyl | 220 | 2-Cyclopentyl-7-ethyl-4-(2-methoxy-ethyl)-imidazo[4,5-e]-s-triazolo[1,5-a]pyrimidin-5-one |
| 157 | Cyclopentyl | — | Cyclopropyl-methyl | H | Ethyl | — | 2-Cyclopentyl-4-cyclopropylmethyl-7-ethyl-imidazo[4,5-e]-s-triazolo[1,5-a]pyrimidin-5-one |
| 158 | Cyclopentyl | — | n-Butyl | H | Methyl | 260 | 4-n-Butyl-2-cyclopentyl-7-methyl-imidazo[4,5-e]-s-triazolo[1,5-a]pyrimidin-5-one |
| 159 | Cyclopentyl | — | 2-Hydroxy-ethyl | H | Ethyl | 285 | 2-Cyclopentyl-7-ethyl-4-(2-hydroxyethyl)-imidazo[4,5-e]-s-triazolo[1,5-a]pyrimidin-5-one |
| 160 | Cyclopentyl | — | 2-Methoxy-ethyl | H | Methyl | 212–214 | 2-Cyclopentyl-4-(2-methoxyethyl)-7-methyl-imidazo[4,5-e]-s-triazolo[1,5-a]pyrimidin-5-one |

The receptor binding values described hereinafter were determined analogously to Ensinger et al. in "Cloning and functional characterisation of human $A_1$ adenosine Receptor—*Biochemical and Biophysical Communications,* Vol 187, No. 2, 919–926, 1992".

The Table which follows contains $K_iA_1$ (human) receptor binding values.

TABLE 2

| Example No.: | $K_iA_1$ [nM] |
|---|---|
| 83 | 8.1 |
| 85 | 6.0 |
| 88 | 2.1 |
| 123 | 3.6 |
| 146 | 2.6 |

The $A_3$ receptor binding values given hereinafter were determined analogously to et al. "Molecular cloning and characterization of the human $A_3$-adenosine receptor" (*Proc. Natl. Acad. Sci. USA* 90, 10365–10369, 1993).

Table 3 contains $KiA_3$ (human) receptor binding values.

TABLE 3

| Example No. | $K_iA_3$ [nM] |
|---|---|
| 34 | 5.6 |
| 64 | 0.9 |
| 81 | 7.2 |
| 149 | 2.2 |
| 151 | 8.3 |

The new compounds of general formula (Ia) to (Id) may be administered orally, transdermally, by inhalation or parenterally. The compounds according to the invention occur as active ingredients in conventional preparations, e.g. in compositions consisting essentially of an inert pharmaceutical carrier and an effective dose of the active substance, such as plain or coated tablets, capsules, lozenges, powders, solutions, suspensions, emulsions, syrups, suppositories, transdermal systems, etc. An effective dose of the compounds according to the invention is between 1 and 100, preferably between 1 and 50, more especially between 5 and 30 mg per dose for oral administration, and between 0.001 and 50, preferably between 0.1 and 10 mg per dose for intravenous or intramuscular use. For inhalation, according to the invention it is appropriate to use solutions which contain 0.01 to 1.0, preferably 0.1 to 0.5% of active substance. For administration by inhalation it is preferable to use powders. It is also possible to use the compounds according to the invention as a solution for infusion, preferably in physiological saline solution or nutrient saline.

The compounds of general formula (I) may be used on their own or in conjunction with other active substances according to the invention, optionally also in conjunction with other pharmacologically active substances. Suitable preparations include for example tablets, capsules, suppositories, solutions, elixirs, emulsions or dispersible powders. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

A therapeutically effective daily dose is between 1 and 800 mg, preferably 10–300 mg per adult.

The Examples which follow illustrate the present invention without restricting its scope:

Examples of Pharmaceutical Formulations

| A) | Tablets | per tablet |
|---|---|---|
| | active substance | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |

-continued

| B) | Tablets | per tablet |
|---|---|---|
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and processed with the remaining corn starch and water to form a granulate which is dried and screened. The sodiumcarboxymethyl starch and the magnesium stearate are added and mixed in and the mixture is compressed to form tablets of a suitable size.

| C) | Coated tablets | per coated tablet |
|---|---|---|
| | active substance | 5 mg |
| | corn starch | 41.5 mg |
| | lactose | 30 mg |
| | polyvinylpyrrolidone | 3 mg |
| | magnesium stearate | 0.5 mg |
| | | 80 mg |

The active substance, corn starch, lactose and polyvinylpyrrolidone are mixed thoroughly and moistened with water. The moist mass is forced through a screen with a mesh size of 1 mm, dried at about 45° C. and the granules are then passed through the same screen. After the magnesium stearate has been mixed in, convex tablet cores with a diameter of 6 mm are compressed in a tablet making machine. The tablet cores thus produced are coated in known manner with a coating consisting essentially of sugar and talc. The finished coated tablets are polished with wax.

| D) | Capsules | per capsule |
|---|---|---|
| | active substance | 50 mg |
| | corn starch | 268.5 mg |
| | magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed. It is cooled to 38° C. and poured into slightly chilled suppository moulds.

| G) | Oral Suspension | |
|---|---|---|
| | Active substance | 50 mg |
| | Hydroxyethylcellulose | 50 mg |
| | Sorbic acid | 5 mg |
| | Sorbitol (70%) | 600 mg |
| | Glycerol | 200 mg |
| | Flavouring | 15 mg |
| | water ad | 5 ml |

Distilled water is heated to 70° C. Hydroxyethylcellulose is dissolved therein with stirring. After the addition of sorbitol solution and glycerol the mixture is cooled to ambient temperature. At ambient temperature, sorbic acid, flavouring and substance are added. The suspension is evacuated with stirring in order to eliminate air.

What is claimed is:
1. A compound of the formula (I):

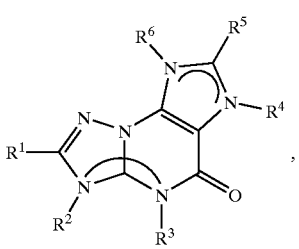

wherein:
$R^1$ denotes hydrogen, or $C_{1-4}$-alkyl, which is optionally substituted by —NHCO—$C_{1-4}$-alkyl, —$NR^7R^8$, hydroxy, $C_{1-4}$-alkyloxy, chlorine or bromine; or
$R^1$ denotes —CHO, —COOH, —COO—$C_{1-4}$-alkyl or phenyl; or
$R^1$ denotes phenyl-$C_{1-3}$-alkyl, which may optionally be substituted by $C_{1-4}$-alkyl, $C_{1-4}$-alkyl-$NR^7R^8$, hydroxy, benzyloxy or fluorine; or
$R^1$ denotes phenyloxy-$C_{1-3}$-alkyl, which may optionally be substituted by methoxy; or
$R^1$ denotes benzyloxy-$C_{1-3}$-alkyl, which may optionally be substituted by methoxy; or
$R^1$ denotes benzyloxybenzyl, benzoyloxymethyl, pyridylcarbonyloxymethyl, cyclohexylmethyl, pyridylmethyl, N-pyrrolylmethyl, N-morpholinomethyl, cyclopentyl or furyl;
$R^2$ or $R^3$ denote $C_{1-5}$-alkyl, $C_{2-4}$-alkenyl or benzyl;
$R^4$ or $R^6$ denote hydrogen, $C_{1-3}$-alkyl, $C_{1-3}$-alkyl-$NR^7R^8$, N-morpholinoethyl or benzyl;
$R^5$ denotes hydrogen, $C_{1-4}$-alkyl, phenyl or benzyl wherein the phenyl ring may optionally be substituted by fluorine; or R⁵ denotes pyridyl, piperidinyl, morpholinyl, piperazinyl, 4benzylpiperazinyl, furyl, tetrahydrofuranyl, tetrahydropyranyl, —NR⁷R⁸, cyclopentyl, cyclohexyl, adamantly, noradamantyl, norbornyl or norbornenyl;

with the proviso that when a nitrogen atom is connected by a double bond, the attached R2, R3, R4 or R6 is not present;

R⁷ denotes hydrogen, $C_{1-4}$-alkyl or pyridyl;

R⁸ denotes hydrogen, $C_{1-4}$-alkyl or pyridyl or a pharmacologically acceptable acid addition salt thereof.

2. A compound of the formula (I), according to claim 1, wherein:

R¹ denotes hydrogen, methyl, which may optionally be substituted by —NH₂, —NHMe, —NMe₂, —N(propyl)₂, —NHAcetyl, hydroxy, methoxy, ethoxy, phenyloxy, methoxyphenyloxy, methoxybenzyloxy, piperazine, methylpiperazine, morpholine, benzoyloxy, pyridylcarbonyloxy, pyridine, pyridylamino, pyrrole or bromine; or R¹ denotes ethyl which is optionally substituted by —NH₂ or hydroxy; or R¹ denotes benzyl which is optionally substituted by hydroxy, methoxy, benzyloxy, dimethylaminoethoxy, N-morpholinoethoxy or fluorine; or R¹ denotes n-propyl, isopropyl, n-butyl, t-butyl, cyclopentyl, cyclohexylmethyl, phenyl, phenylethyl, —CHO, —COOH, —COOMe, COOEt, COOPropyl, COOButyl or furan;

R² or R³ denote methyl, ethyl, n-propyl, isopropyl, n-butyl, isobutyl, t-butyl, allyl, butenyl, n-pentyl, propargyl or benzyl;

R⁴ or R⁶ denote hydrogen, methyl, n-propyl or benzyl; or

R⁴ or R⁶ denote ethyl which is optionally substituted by morpholine;

R⁵ denotes hydrogen, methyl, ethyl, n-propyl, isopropyl, n-butyl, t-butyl, phenyl, benzyl, pyridyl, —NH₂, —NHMe, —NMe₂, piperidinyl, morpholinyl; or R⁵ denotes piperazinyl which is optionally substituted by methyl or benzyl; or R⁵ denotes furyl, tetrahydrofuranyl, tetrahydropyranyl, cyclopentyl, cyclohexyl, adamantyl, noradamantyl, norbornanyl or norbornenyl, or a pharmacologically acceptable acid addition salt thereof.

3. A compound of the formula (I), according to claim 1, wherein:

R¹ denotes hydrogen, methyl which is optionally substituted by —NMe₂, hydroxy, methoxy, ethoxy, phenyloxy, methoxyphenyloxy, methoxybenzyloxy, morpholine, benzoyloxy, pyridylcarbonyloxy, pyridine, pyridylamino or pyrrole; or R¹ denotes ethyl, n-propyl, isopropyl, n-butyl, t-butyl, cyclopentyl, cyclohexylmetyl or benzyl which is optionally be substituted by hydroxy, methoxy, dimethylaminoethoxy or fluorine; or R¹ denotes phenyl, phenylethyl, —COOH, —COOMe or furan;

R² or R³ denote methyl, ethyl, n-propyl, isopropyl, n-butyl, isobutyl, t-butyl, n-pentyl, allyl, butenyl, propargyl or benzyl;

R⁴ or R⁶ denote hydrogen; and,

R⁵ denotes hydrogen, ethyl, n-propyl, isopropyl, n-butyl, t-butyl, phenyl, benzyl, pyridine, piperidine, morpholine, piperazine, 4-benzylpiperazinyl, tetrahydrofuranyl, tetrahydropyranyl, —NMe₂, cyclopentyl, cyclohexyl, adamantyl, noradamantyl, norbornanyl or 5-norbornenyl, or a pharmacologically acceptable acid addition salt thereof.

4. A compound of the formula (I), according to claim 1, wherein:

R¹ denotes methyl, which is optionally substituted by —NH₂, —NHMe, —N(iso-propyl)₂, —NHAcetyl, hydroxy, phenyloxy, methylpiperazine or pyrrole; or R¹ denotes ethyl which is optionally substituted by —NH₂ or hydroxy; or R¹ denotes benzyl which is optionally substituted by hydroxy, methoxy, benzyloxy, dimethylaminoethoxy, N-morpholinoethoxy or fluorine; or R¹ denotes cyclopentyl phenylethyl, —COOH, —COOPropyl, —COOButyl or furan;

R² or R³ denote ethyl, n-propyl, isopropyl, n-butyl, isobutyl, n-pentyl, allyl, butenyl or propargyl;

R⁴ or R⁶ denote hydrogen, methyl or ethyl, which is substituted by morpholine; and, R⁵ denotes methyl, ethyl, n-propyl, t-butyl, cyclopentyl or norbornenyl, or a pharmacologically acceptable acid addition salt thereof.

5. A compound of the formula (I), according to claim 1, wherein:

R¹ denotes methyl, which is optionally substituted by phenyloxy or pyrrole; or

R¹ denotes benzyl which is optionally substituted by hydroxy, methoxy, dimethylaminoethoxy or fluorine; or R¹ denotes cyclopentyl, furan or phenylethyl;

R² or R³ denote ethyl, n-propyl, allyl or propargyl;

R⁴ or R⁶ denote hydrogen; and,

R⁵ denotes methyl, n-propyl, t-butyl, cyclopentyl or norbornenyl, or a pharmacologically acceptable acid addition salt thereof.

6. A compound of the formula (Ia) or (Ib)

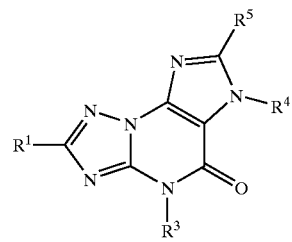

(Ia)

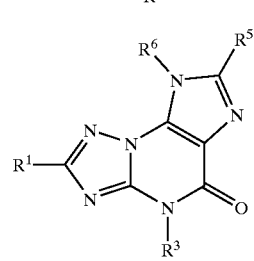

(Ib)

wherein $R^1$, $R^2$, $R^3$, $R^4$, $R^5$ and $R^6$ are defined as set forth in claim 1, 2, 3, 4 or 5.

7. A compound of the formula (Ia)

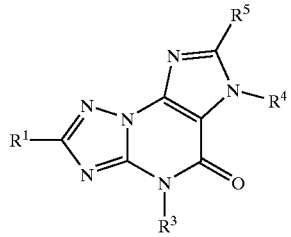

(Ia)

wherein $R^1$, $R^2$, $R^3$, $R^4$, $R^5$ and $R^6$ are defined as set forth in claim 1, 2, 3, 4 or 5.

8. A compound of the formula (Ib)

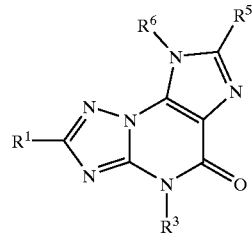

(Ib)

wherein $R^1$, $R^2$, $R^3$, $R^4$, $R^5$ and $R^6$ are defined as set forth in claim 1, 2, 3, 4 or 5.

9. A pharmaceutical composition comprising a compound of the formula (I) in accordance with claim 1, 2, 3, 4 or 5.

10. A pharmaceutical composition comprising a compound of the formula (Ia) in accordance with claim 7.

11. A pharmaceutical composition comprising a compound of the formula (Ib) in accordance with claim 8.

* * * * *